US011285126B2

(12) United States Patent
Bannenberg et al.

(10) Patent No.: US 11,285,126 B2
(45) Date of Patent: Mar. 29, 2022

(54) OILS WITH ANTI-INFLAMMATORY ACTIVITY CONTAINING NATURAL SPECIALIZED PRORESOLVING MEDIATORS AND THEIR PRECURSORS

(71) Applicant: Solutex NA LLC, Miami, FL (US)

(72) Inventors: Gerhardus Lucas Bannenberg, Manzanares el Real (ES); Charles Nicholas Serhan, Needham, MA (US); Fernando Moreno Egea, Alcobendas (ES)

(73) Assignee: Solutex NA LLC, Miami, FL (US)

( * ) Notice: Subject to any disclaimer, the term of this patent is extended or adjusted under 35 U.S.C. 154(b) by 0 days.

(21) Appl. No.: 16/882,910

(22) Filed: May 26, 2020

(65) Prior Publication Data

US 2020/0281883 A1    Sep. 10, 2020

Related U.S. Application Data

(63) Continuation of application No. 16/297,240, filed on Mar. 8, 2019, which is a continuation of application No. 15/935,913, filed on Mar. 26, 2018, now abandoned, which is a continuation of application No. 14/400,198, filed as application No. PCT/US2013/040314 on May 9, 2013, now Pat. No. 10,568,858.

(60) Provisional application No. 61/645,281, filed on May 10, 2012.

(51) Int. Cl.
| | | |
|---|---|---|
| *A61K 35/60* | (2006.01) | |
| *A61K 31/202* | (2006.01) | |
| *A61K 31/557* | (2006.01) | |
| *A61K 35/612* | (2015.01) | |
| *A61K 35/618* | (2015.01) | |
| *A61K 36/02* | (2006.01) | |

(52) U.S. Cl.
CPC .......... *A61K 31/202* (2013.01); *A61K 31/557* (2013.01); *A61K 35/60* (2013.01); *A61K 35/612* (2013.01); *A61K 35/618* (2013.01); *A61K 36/02* (2013.01)

(58) Field of Classification Search
None
See application file for complete search history.

(56) References Cited

U.S. PATENT DOCUMENTS

| | | |
|---|---|---|
| 4,235,871 A | 11/1980 | Papahadjopoulos et al. |
| 4,501,728 A | 2/1985 | Geho et al. |
| 4,837,028 A | 6/1989 | Allen |
| 4,966,876 A | 10/1990 | Sankaran |
| 5,133,902 A | 7/1992 | Sankaran |
| 5,776,978 A | 7/1998 | Bruzzese |
| 6,284,268 B1 | 9/2001 | Mishra et al. |
| 7,259,006 B2 | 8/2007 | Komazawa et al. |
| 7,884,131 B2 * | 2/2011 | Arterburn ................. A61P 7/10 514/549 |
| 8,735,111 B2 | 5/2014 | Vanhercke et al. |
| 9,238,634 B2 | 1/2016 | Arita et al. |
| 10,653,703 B2 | 5/2020 | Serhan et al. |
| 2009/0023808 A1 | 1/2009 | Raman et al. |
| 2009/0099260 A1 | 4/2009 | Senanayake et al. |
| 2009/0318394 A1 | 12/2009 | Nauroth et al. |
| 2011/0190389 A1 | 8/2011 | Arterburn et al. |
| 2012/0059061 A1 | 3/2012 | Arita et al. |
| 2013/0261180 A1 | 10/2013 | Gillies et al. |
| 2015/0126602 A1 | 5/2015 | Bannenberg et al. |
| 2015/0196521 A1 | 7/2015 | Manku et al. |

FOREIGN PATENT DOCUMENTS

| | | |
|---|---|---|
| CN | 1202068 | 1/2004 |
| CN | 1469858 | 1/2004 |
| CN | 100348184 | 12/2005 |
| JP | H01169354 | 7/1989 |
| JP | 6282586 | 7/2014 |
| KR | 2013/0135839 | 12/2013 |
| WO | WO 2002/102364 | 12/2002 |
| WO | WO 2005/089744 | 9/2005 |
| WO | WO 2006/055965 | 5/2006 |
| WO | WO 2013/170006 | 1/2014 |
| WO | WO 2014/209132 | 12/2014 |

OTHER PUBLICATIONS

Mori et al. (1997) Artheriosclerosis, Thrombosis and Vacular Biology, vol. 17, Issue 2: 279-286. (Year: 1997).*
Serhan et al. (2011) Chem. Rev. 111: 5922-5943. (Year: 2011).*
Revilla et al. (1998) J. Agric. Food Chem. 46: 4592-4597. (Year: 1998).*
Raskin et al. (2004) Current Pharmaceutical Design, 10: 3419-3429. (Year: 2004).*
Neuhofer et al. (2013) Diabetes, 62: 1945-1956. (Year: 2013).*
Wu et al. (2004) Ann. N.Y. Acad. Sci. 1031: 422-424. (Year: 2004).*
Paragraphs 13, 14 and 51 of the Transcript which accompanies Documento di Ammsisione (Pharmanutra) online at https://docplayer.it/54881332-Documento-di-ammissione.html#showfull text, (with English translation).

(Continued)

*Primary Examiner* — Russell G Fiebig
(74) *Attorney, Agent, or Firm* — Perkins Coie LLP

(57) ABSTRACT

The present invention encompasses oils that have anti-inflammatory or resolution-stimulating activity that contain or are enriched with Specialized Proresolving Mediators (SPM) or SPM precursors, which originate from an oil obtained from organisms containing long chain omega-3 polyunsaturated fatty acids, such as fish, crustaceae, algae, and mollusks. The invention also encompasses a method for the production of these oils, and the utilization of the oils for nutritional supplements, pharmaceutical formulations, and cosmetic formulations, which can be employed for treating an inflammatory condition.

10 Claims, 11 Drawing Sheets

(56) References Cited

OTHER PUBLICATIONS

Artero et al., "Fish Oil Metabolites: Translating Promising Findings From Bench to Bedside to Reduce Cardiovascular Disease," J Glycomics Lipidomics, 2(1):1000106 (publication date: Feb. 27, 2012).
Lovaza, Generic Name: omega-3-acid ethyl esters Brand Name: Lovaza, https://www.rxlist.com/lovaza-drug.htm.
Shaikh et al., "n-3 Polyunsaturated fatty acids exert immunomodulatory effects on lymphocytes by targeting plasma membrane molecular organization," Mol Aspects Med,33(1):46-54 (epublication date: Oct. 19, 2011).
Ariel et al., "Apoptotic neutrophils and T cells sequester chemokines during immune response resolution through modulation of CCR5 expression," Nat Immunol. 7(11):1209-16 (publication date: Nov. 2006, epublication date: Oct. 1, 2006).
Arita et al., "Resolvin E1, an endogenous lipid mediator derived from Omega-3 eicosapentaenoic acid, protects against 2,4,6-trinitrobenzene sulfonic acid-induced colitis," Proc Natl Acad Sci USA. 102(21):7671-76 (publication date: May 24, 2005, epublication date: May 12, 2005).
Arita et al., "Stereochemical assignment, anti-inflammatory properties, and receptor for the omega-3 lipid mediator resolvin E1," J Exp Med. 201(5):713-22 (publication date: Mar. 7, 2005).
Armenta et al., "Transesterification of Fish Oil to Produce Fatty Acid Ethyl Esters Using Ultrasonic Energy," J Am Oil Chern Soc. 84:1045-1052 (publication date: Nov. 2007, epublication date: Sep. 18, 2007).
Aveldaño et al., "Synthesis of hydroxy fatty acids from 4, 7, 10, 13, 16, 19-[1 -14C] docosahexaenoic acid by human platelets," J Biol Chem 258(15):9339-43 (publication date: Aug. 10, 1983).
Bannenberg et al., "Molecular circuits of resolution: formation and actions of resolvins and protectins," J. Immunol. 174(7):4345-55 (publication date: Apr. 1, 2005).
Bannenberg et al., "Specialized pro-resolving lipid mediators in the inflammatory response: An update," Biochim Biophys Acta. 1801(12):1260-73 (publication date: Dec. 2010, epublication date: Aug. 10, 2010).
Barden et al., "Specialised pro-resolving mediators of inflammation in inflammatory arthritis," Prostaglandins, Leukotrienes and Essential Fatty Acids 107:24-29 (publication date: Apr. 2016, epublication date: Mar. 9, 2016).
BASF Safety Data Sheet. "Omega Oil 1812 TG Gold," Revision Date Oct. 24, 2018, pp. 1-9 (2018).
Bento et al., "Omega-3 fatty acid-derived mediators 17(R)-hydroxy docosahexaenoic acid, aspirin-triggered resolvin D1 and resolvin D2 prevent experimental colitis in mice," Journal of Immunology, 187(4):1957-69. (publication date: Aug. 15, 2011, epublication date: Jul. 1, 2011).
Biswas et al., "Macrophage plasticity and interaction with lymphocyte subsets: cancer as a paradigm," Nature Immunol. 11, 889-896. (publication date: Oct. 2010, epublication date: Sep. 20, 2010).
Cao et al., "A specific role of integrin Mac-1 in accelerated macrophage efflux to the lymphatics," Blood. 106(9):3234-41. (publication date: Nov. 1, 2005, epublication date: Jul. 7, 2005).
Chiu et al., "Omega-6 docosapentaenoic acid-derived resolvins and 17-hydroxydocosahexaenoic acid modulate macrophage function and alleviate experimental colitis," Inflamm Res 61(9):967-76 (publication date: Sep. 2012, epublication date: May 23, 2012).
Clària et al., "Diversity of lipid mediators in human adipose tissue depots," Am J Physiol Cell Physiol 304(12):C1141-9 (publication date: Jun. 2013. epublication date: Jan. 30, 2013).
Clària et al., "Resolvin D1 and resolvin D2 govern local inflammatory tone in obese fat," J Immunol. 189(5):2597-605 (publication date: Sep. 1, 2012, Jul. 27, 2012).
Colas et al., "Identification and signature profiles for pro-resolving and inflammatory lipid mediators in human tissue," Am J Physiol Cell Physiol. 307(1):C39-54 (publication date: Jul. 1, 2014, epublication date: Apr. 2, 2014).

Cunningham, "Proinflammatory Properties of Unsaturated Fatty Acids and Their Monohydroxy Metabolites," Prostaglandins 30(3):498-509 (publication date: Sep. 1985).
Dallegri et al., "Tissue injury in neutrophilic inflammation," Inflamm Res. 46(10):382-391 (publication date: Oct. 1997) (Abstract only).
Dalli et al., "Novel n-3 Immunoresolvents: Structures and Actions," Scientific Reports 3. Article No. 1940 doi:10.1038/srep01940 (publication date: Jun. 5, 2013).
Dalli et al., "Resolvin D3 and Aspirin Triggered Resolvin D3 are Potent Immunoresolvents," Chem Biol. 20(2):188-201 (publication date: Feb. 21, 2013).
Dalli et al., "Specific lipid mediator signatures of human phagocytes: microparticles stimulate macrophage efferocytosis and pro-resolving mediators," Blood. 120(15):e60-e72 (publication date: Oct. 11, 2012, epublication date: Aug. 17, 2012).
Dangi et al., "Biogenic Synthesis, Purification, and Chemical Characterization of Anti-inflammatory Resolvins Derived from Docosapentaenoic Acid (DPAn-6)," Journal of Biological Chemistry, 284(22):14744-14759 (publication date: May 29, 2009, epublication date: Mar. 26, 2009).
Endo et al., "18-HEPE and n-3 fatty acid metabolite released by macrophages, prevents pressure overload-induced maladaptive cardiac remodeling," J Exp Med. 211(8):1673-87 (publication date: Jul. 28, 2014, epublication date: Jul. 21, 2014).
Fischer et al., "Uptake, release and metabolism of docosahexaenoic acid (DHA, c22:6 omega 3) in human platelets and neutrophils," Biochem Biophys Res Commun 120(3):907-18 (publication date: May 16, 1984).
Fogh et al., "Improvement of psoriasis vulgaris after intralesional injections of 15-hydroxyeicosatetraenoic acid (15-HETE)," J Am Acad Dermatol 18(Issue 2, Part 1):279-285 (publication date: Feb. 1988) (part of this study was published in a letter to the editor in Laneet in 1986).
Fredman et al., "Impaired phagocytosis in localized aggressive periodontitis: rescue by Resolvin E1," PLoS One 6(9):e24422 (epublication date: Sep. 14, 2011).
Gladyshev et al., "Production of EPA and DHA in aquatic ecosystems and their transfer to the land," Prostaglandins Other Lipid Mediat. 107:117-26 (publication date: Dec. 2013, epublication date: Mar. 14, 2013) (Abstract only).
Gleissman et al., "Docosahexaenoic acid metabolome in neural tumors: identification of cytotoxic intermediates," FASEB J 24(3):906-15 (publication date: Mar. 2010, epublication date: Nov. 4, 2009).
González-Périz et al., "Docosahexaenoic acid (DHA) blunts liver injury by conversion to protective lipid mediators: protectin D1 and 17S-hydroxy-DHA," (14):2537-9 (publication date: Dec. 2006, epublication date: Oct. 20, 2006).
Gordon, S., "Alternative activation of macrophages," Nat Rev Immunol. (1):23-35 (publication date: Jan. 2003) (Abstract only).
Gross et al., "Bioluminescence imaging of myeloperoxidase activity in vivo," Nat. Med. 15(4):455-61 (publication date: Apr. 2009, epublication date: Mar. 22, 2009).
Han et al., "Limiting inflammatory responses during activation of innate immunity," Nat. Immunol. 6(12):1198-1205 (publication date: Dec. 2005) (Abstract only).
Haraldsson et al., "Separation of Eicosapentaenoic Acid and Docosahexaenoic Acid in Fish Oil by Kinetic Resolution Using Lipase," J. Am. Oil Chem. Soc. 75:1551-1556 (publication date: Nov. 1998).
Haraldsson et al., "The Preparation of Concentrates of Eicosapentaenoic Acid and Docosahexaenoic Acid by Lipase-Catalyzed Transesterification of Fish Oil with Ethanol," J. Am. Oil Chem. Soc. 74(11):1419-1424 (publication date: Nov. 1997).
Haslett C., "Resolution of acute inflammation and the role of apoptosis in the tissue fate of granulocytes," Clin Sci (Lond). 83(6):639-48 (publication date: Dec. 1992).
Hawthorne et al., "High dose eicosapentaenoic acid ethyl ester: effects on lipids and neutrophil leukotriene production in normal volunteers," Br. J. Clin. Pharmac. 30(2):187-194 (publication date: Aug. 1990).

(56) References Cited

OTHER PUBLICATIONS

Hills et al., "Enzymatic Fractionation of Fatty Acids: Enrichment of γ-Linolenic Acid and Docosahexaenoic Acid by Selective Esterification Catalyzed by Lipases," J. Am. Oil Chem. Soc. 67(9):561-564 (publication date: Sep. 1990).
Hong et al., "Novel docosatrienes and 17S-resolvins generated from docosahexaenoic acid in murine brain, human blood, and glial cells," J Biol Chem. 278(17):14677-87 (publication date: Apr. 25, 2003, epublication date: Feb. 17, 2003).
Hong et al., "Rainbow trout (*Oncorhynchus mykiss*) brain cells biosynthesize novel docosahexaenoic acid-derived resolvins and protectins-Mediator Lipidomic analysis," Prostaglandins Other Lipid Mediat. 78(1-4):107-16 (publication date: Dec. 2005, epublication date: Jun. 13, 2005) (Abstract only).
Huynh et al., "Phosphatidylserine-dependent ingestion of apoptotic cells promotes TGF-β1 secretion and the resolution of inflammation," J Clin Invest. 109(1):41-50. (publication date: Jan. 1, 2002).
International Search Report and Written Opinion dated Dec. 2, 2016 for International Application No. PCT/US2016/050397.
International Search Report and Written Opinion dated Oct. 31, 2013 for International Application No. PCT/US2013/40314.
Isobe et al., "Identification and structure determination of novel anti-inflammatory mediator resolvin E3, 17,18-dihydroxyeicosapentaenoic acid," J Biol Chem, 287(13):10525-34 (publication date: Mar. 23, 2012).
Kadota et al., "Separation of Polyunsaturated Fatty Acids by Chromatography Using a Silver-Loaded Spherical Clay. I. Pilot-Scale Preparation of High purity Docosahexaenoic Acid by Supercritical Fluid Chromatography," Journal of Oleo Science 46(4):397-403 (1997) (with English translation).
Kohli et al., "Resolvins and protectins: mediating solutions to inflammation," Br. J. Pharmacol. 158(4):960-971 (publication date: Oct. 2009, epublication date: Jul. 7, 2009).
Köhnke et al., "Acetylsalicylic Acid Reduces the Severity of Dextran Sodium Sulfate-Induced Colitis and Increases the Formation of Anti-Inflammatory Lipid Mediators," Biomed Res Int. Article ID No. 748160 (epublication date: Sep. 8, 2013).
Kremer "n-3 Fatty acid supplements in rheumatoid arthritis," Am. J. Clin. Nutr. 71(suppl):349S-351S (publication date: Jan. 2000).
Krishnamurthy et al., "Total synthesis and bioactivity of 18(R)-hydroxyeicosapentaenoic acid," J Org Chem, 76(13):5433-7 (publication date: Jul. 1, 2011).
Kuo et al., "Anti-inflammatory Effects of Supercritical Carbon Dioxide Extract and Its Isolated Carnosic Acid from Rosmarinus officinalis Leaves," J. Agric. Food Chem. 59:3674-85 (publication date: Apr. 27, 2011, epublication date: Mar. 4, 2011).
Levy et al., "Lipid mediator class switching during acute inflammation: signals in resolution," Nat Immunol. 2(7):612-9 (publication date: Jul. 2001) (Abstract only).
Levy et al., "Resolution of acute inflammation in the lung," Annu. Rev. Physiol. 76:467-492 (epublication date: Dec. 2, 2013).
Lima-Garcia et al., "The precursor of resolvin D series and aspirin-triggered resolvin D1 display antihyperalgesic properties in adjuvant-induced arthritis in rats," Br J Pharmacol. 164(2):278-293 (publication date: Sep. 2011).
Lin et al., "Enrichment of n-3 PUFA contents on triglycerides of fish oil by trans-esterification under supercritical conditions," Biochemical Engineering Journal 29 (Issues 1-2):27-34 (Apr. 1, 2006) (epublication date: Jul. 11, 2005).
López-Vicario et al., "Inhibition of soluble epoxide hydrolase modulates inflammation and autophagy in obese adipose tissue and liver: role for Omega-3 epoxides," Proc Natl Acad Sci U S A. 112(2):536-41 (epublication date: Dec. 30, 2014).
Maehr et al., "Enzymic Enhancement of n-3 Fatty Acid Content in Fish Oils," J. Am. Oil Chem. Soc. 71(5):463-467 (May 1994) (This paper was presented at the 82nd AOCS Annual Meeting, May 12-15, 1991).
Mas et al., "Resolvins D1, D2, and other mediators of self-limited resolution of inflammation in human blood following n-3 fatty acid supplementation," Clinical Chemistry 58:10:1476-84 (publication date: Oct. 2012, epublication date: Aug. 21, 2012).
Masoodi et al., "Simultaneous lipidomic analysis of three families of bioactive lipid mediators leukotrienes, resolvins, protectins and related hydroxy-fatty acids by liquid chromatography/electrospray tandem mass spectrometry," Rapid Commun Mass Spectrom. 22(2):75-83 (publication date: Sep. 18, 2008).
McKimmie et al., "Leucocyte expression of the chemokine scavenger D6," Biochem Soc Trans. 34(Pt 6):1002-4 (publication date: Dec. 2006).
Metlay et al., "Time course of symptom resolution in patients with community-acquired pneumonia," Respir Med. 92(9):1137-42 (publication date: Sep. 1998).
Miller et al., "Dietary Supplementation with Ethyl Ester Concentrates of Fish Oil (n-3) and Borage Oil (n-6) Polyunsaturated Fatty Acids Induces Epidermal Generation of Local Putative Anti-Inflammatory Metabolites," J. Invest. Dermatol. 96(1):98-103 (Jan. 1991).
Miyahara et al., "D-series resolvins attenuate vascular smooth muscle cell activation and neointimal hyperplasia following vascular injury," FASEB J. 27:2220-2232 (publication date: Jun. 2013, epublication date: Feb. 13, 2013).
Murphy et al., "Fatty acid and sterol composition of frozen and freeze-dried New Zealand Green Lipped Mussel (*Perna canaliculus*) from three sites in New Zealand," Asia Pacific J. Clin. Nutr. 12(1):50-60 (publication date: Mar. 2003).
Nagakura et al., "Dietary supplementation with fish oil rich inomega-3 polyunsaturated fatty acids in children with bronchial asthma," Eur Respir J, 16(5):861-5 (publication date: Nov. 200).
Neuhofer et al., "Impaired local production of proresolving lipid mediators in obesity and 17-HDHA as a potential treatment for obesity-associated inflammation," 62(6):1945-56 (publication date: Jun. 2013, epublication date: Jan. 24, 2013).
Norling et al., "Cutting edge: Humanized nano-proresolving medicines mimic inflammation-resolution and enhance wound healing," J Immunol 6186(10):5543-7 (publication date: May 15, 2011, epublication date: Apr. 1, 2011).
Ogawa et al., "Total synthesis and bioactivity of resolvin E2," Org Lett, 11(16):3602-5 (publication date: Aug. 20, 2009).
Oh et al., "Chiral lipidomics of E-series resolvins: aspirin and the biosynthesis of novel mediators," Biochim Biophys Acta. 1811(11):737-47 (publication date: Nov. 2011, epublication date: Jun. 16, 2011).
Oh et al., "Pro-resolving actions and stereoselective biosynthesis of 18S E-series resolvins in human leukocytes and murine inflammation," J Clin Invest. 121(2):569-81 (publication date: Feb. 2011, epublication date: Jan. 4, 2011).
Oh et al., "Resolvin E2: formation and impact in inflammation resolution," J Immunol. 188(9):4527-34 (publication date: May 1, 2012, epublication date: Mar. 26, 2012).
Ohira et al., "Resolvin E1 receptor activation signals phosphorylation and phagocytosis," J. Biol. Chem. 285(5):3451-61 (publication date: Jan. 29, 2010, epublication date: Nov. 11, 2009).
Perretti et al., "Supercritical carbon dioxide fractionation offish oil fatty acid ethyl esters," J. of Supercritical Fluids 40:349-353 (publication date: Apr. 2007, epublication date: Aug. 30, 2006).
Petrie et al., "Metabolic engineering plant seeds with fish oil-like levels of DHA," PLoS One. 7(11):e49165 (epublication date: Nov. 7, 2012).
Pettitt et al., "Lipoxins are major lipoxygenase products of rainbow trout macrophages," FEBS Lett 259(1):168-70 (publication date: Dec. 18, 1989) (Abstract only).
Psychogios et al., "The human serum metabolome," PLoS ONE. 6(2):e16957 (publication date: Feb. 16, 2011).
Raatz et al., "Baking reduces prostaglandin, resolvin, and hydroxy-fatty acid content of farm-raised Atlantic salmon (*Salmo salar*)," J Agric Food Chem 59(20):11278-86 (epublication date: Oct. 4, 2011).
Ramon et al., "Specialized proresolving mediators enhance human B cell differentiation to antibody-secreting cells," J Immunol 189(2):1036-42 (publication date: Jul. 15, 2012, epublication date: Jun. 18, 2012).

(56) References Cited

OTHER PUBLICATIONS

Ramon et al., "The specialized proresolving mediator 17-HDHA enhances the antibody-mediated immune response against influenza virus: a new class of adjuvant?," J Immunol. 193(12):6031-40 (publication date: Dec. 15, 2014, epublication date: Nov. 12, 2014).
Rhodes et al., "The sunburn response in human skin is characterized by sequential eicosanoid profiles that may mediate its early and late phases," FASAB J. 23(11):3947-56 (publication date: Nov. 2009, epublication date: Jul. 7, 2009).
Salas, "Fish oil: The quintessential fatty acid Fish Oil consumption reduces illness and effects of aging," Argo Food Industry Hi-Tech, 22(1):30-32 (publication date: Jan. 2011).
Sapieha et al., "5-Lipoxygenase metabolite 4-HDHA is a mediator of the antiangiogenic effect of ω-3 polyunsaturated fatty acids," Sci Transl Med 3(69):69ra12 (publication date: Feb. 9, 2011).
Savill et al., "Granulocyte clearance by apoptosis in the resolution of inflammation," Semin Cell Biol. 6(6):385-93 (publication date: Dec. 1995) (Abstract only).
Sawazaki et al., "Lipoxygenation of docosahexaenoic acid by the rat pineal body," J Neurochem 62(6):2437-47 (publication date: Jun. 1994).
Schwab et al., "Resolvin E1 and protectin D1 activate inflammation-resolution programs," Nature. 447:869-74 (publication date: Jun. 14, 2007).
Serhan et al., "Endogenous pro-resolving and anti-inflammatory lipid mediators: A new pharmacologic genus," Br J Pharmacol 153:S200-15 (publication date: Mar. 2008, epublication date: Oct. 29, 2007).
Serhan et al., "Lipoxins: novel series of biologically active compounds formed from arachidonic acid in human leukocytes," Proc Nati Acad Sci USA, 81(17):5335-39 (publication date: Sep. 1984).
Serhan et al., "Novel functional sets of lipid-derived mediators with antiinflammatory actions generated from omega-3 fatty acids via cyclooxygenase 2-nonsteroidal antiinflammatory drugs and transcellular processing," J Exp Med. 192(8):1197-204 (publication date: Oct. 16, 2000).
Serhan et al., "Resolution of inflammation: the beginning programs the end," Nat Immunol. 6(12):1191-97 (publication date: Dec. 2005) (Abstract only).
Serhan et al., "Resolution phase lipid mediators of inflammation: agonists of resolution," Curr Opin Pharmacol. 13(4):632-40 (publication date: Aug. 13, 2013, epublication date: Jun. 6, 2013).
Serhan et al., "Resolving inflammation: dual anti-inflammatory and pro-resolution lipid mediators," Nat Rev Immunol. 8(5):349-61. (publication date: May 2008).
Serhan et al., "Resolvins and Protectins in Inflammation Resolution," Chemical Reviews, 111:5922-5943 (publication date: Oct. 12, 2011, epublication date: Jul. 18, 2011).
Serhan et al., "Resolvins: a family of bioactive products of Omega-3 fatty acid transformation circuits initiated by aspirin treatment that counter proinflammation signals," J Exp Med. 196(8):1025-37 (publication date: Oct. 21, 2002).
Serhan et al., "Resolvins and Protectins in Inflammation-Resolution," Chem Rev. 111(10):5922-43 (publication date: Oct. 12, 2011, epublication date: Jul. 18, 2011).
Serhan, "Novel eicosanoid and docosanoid mediators: Resolvins, docosatrienes, and neuroprotectins," Curr Opin Clin Nutr Metab Care. 8(2):115-21 (publication date: Mar. 2005).
Serhan, "Novel pro-resolving lipid mediators are leads for resolution physiology," Nature. 510(7503):92-101 (publication date: Jun. 5, 2014).
Shearer et al., "Detection of omega-3 oxylipins in human plasma and response to treatment with omega-3 acid ethyl esters," J Lipid Res 51(8):2074-2081 (publication date: Aug. 2010, epublication date: Aug. 11, 2009).
Singer et al., "Anti-inflammatory properties of omega-3 fatty acids in critical illness: novel mechanisms and an integrative perspective," Intensive Care Med. 34:1580-92 (publication date: Sep. 2008, epublication date: May 7, 2008).

Spite et al., "Novel lipid mediators promote resolution of acute inflammation: Impact of aspirin and statins," Cir Res 107(10):1170-84 (publication date: Nov. 12, 2010).
Spite et al., "Resolvins, specialized proresolving lipid mediators, and their potential roles in metabolic diseases," Cell Metab 19(1):21-36 (publication date: Jan. 7, 2014, epublication date: Nov. 14, 2013).
Stuart et al., "Apoptotic cells and innate immune stimuli combine to regulate macrophage cytokine secretion," J Immunol. 171(5):2610-15 (publication date: Sep. 1, 2003).
Sun et al., "Resolvin D1 and its aspirin-triggered 17R epimer: stereochemical assignments, anti-inflammatory properties, and enzymatic inactivation," J Biol Chem. 282(13):9323-34 (publication date: Mar. 30, 2007, epublication date: Jan. 23, 2007).
Tabas et al., "Anti-inflammatory therapy in chronic disease: challenges and opportunities," Science. 339(6116):166-72 (Jan. 11, 2013).
Ternowitz et al., "15-Hydroxyeicosatetraenoic acid (15-HETE) specifically inhibits LTB4-induced chemotaxis of human neutrophils," Skin Pharmacol 1(2):93-9 (1988).
Ternowitz et al., "15-Hydroxyeicosatetraenoic acid (15-HETE) specifically inhibits the LTB4-induced skin response," Arch Dermatol Res (281:401-405 (1989).
Titos et al., "Resolvin D1 and its precursor docosahexaenoic acid promote resolution of adipose tissue inflammation by eliciting macrophage polarization toward an M2-like phenotype," J Immunol. 187(10):5408-18 (publication date: Nov. 15, 2011, epublication date: Oct. 17, 2011).
Uddin et al., "Resolvins: Natural agonists for resolution of pulmonary inflammation," Progress in Lipid Research. 50:75-88 (publication date: Jan. 2011, epublication date: Sep. 29, 2010).
Uller et al., "Resolution of airway disease: removal of inflammatory cells through apoptosis, egression or both?" Trends Pharmacol Sci. 27(9):461-6 (publication date: Sep. 2006, epublication date: Jul. 31, 2006) (Abstract only).
VanRollins et al., "Oxidation of docosahexaenoic acid by rat liver microsomes," J Biol Chem 259(9):5776-83 (publication date: May 10, 1984).
Varani et al., "Mechanisms of endothelial cell injury in acute inflammation," Shock. 2(5):311-9 (publication date: Nov. 1994) (Abstract only).
Wagner et al., "Soluble epoxide hydrolase inhibition, epoxygenated fatty acids and nociception," Prostaglandins Other Lipid Mediat. 96(1-4):76-83 (publication date: Nov. 2011, epublication date: Aug. 10, 2011).
Walker et al., "Regulation of neutrophil apoptosis and removal of apoptotic cells," Curr Drug Targets Inflamm Allergy. 4(4):447-54 (publication date: Aug. 2005) (Abstract only).
Wang et al., "A process for the synthesis of PUFA-enriched triglycerides from high-acid crude fish oil," J. Food Engineering 109:366-71 (epublication date: Nov. 25, 2011).
Wang et al., "Hydroxyeicosapentaenoic acids and epoxyeicosatetraenoic acids attenuate early occurance of nonalcoholic fatty liver disease," British Journal of Pharmacology, 174:2358-72 (epublication date: Jun. 9, 2017).
Weiss, "Tissue destruction by neutrophils," N Engl J Med 320(6):365-76 (publication date: Feb. 9, 1989) (Abstract only).
Weitz et al., "Fish Oil for the Treatment of Cardiovascular Disease," Cardiol Rev. 15(5):258-63 (publication date: Sep.-Oct. 2010).
Weylandt et al., "Lipoxins and resolvins in inflammatory bowel disease," Inflammatory Bowel Diseases. 13(6):797-9 (publication date: Jun. 2007) (Abstract only).
Weylandt et al., "Omega-3 fatty acids and their lipid mediators: towards an understanding of resolvin and protectin formation," Prostaglandins Other Lipid Mediat 97(3-4):73-82 (publication date: Mar. 2012, epublication date: Feb. 3, 2012).
Weylandt et al., "Suppressed liver tumorigenesis in fat-1 mice with elevated omega-3 fatty acids is associated with increased omega-3 derived lipid mediators and reduced TNF-α," Carcinogenesis. 32(6):897-903 (publication date: Jun. 2011, epublication date: Mar. 17, 2011).
White et al., "Resolution of bronchial inflammation is related to bacterial eradication following treatment of exacerbations of chronic bronchitis," Thorax. 58(8):680-85 (publication date: Aug. 2003).

(56) References Cited

OTHER PUBLICATIONS

Willoughby et al., "Resolution of inflammation," Intl J Immunopharmacol. 22(12):1131-5 (publication date: Dec. 2000) (Abstract only).

Yamamoto et al., "4-Hydroxydocosahexaenoic acid, a potent peroxisome proliferator-activated receptor gamma agonist alleviates the symptoms of DSS-induced colitis," Biochem Biophys Res Commun 367(3):566-72 (publication date: Mar. 14, 2008, epublication date: Jan. 10, 2008).

Yang et al., "Metabolomics-lipidomics of eicosanoids and docosanoids generated by phagocytes," Curr Protoc Immunol. Chapter 14, Unit 14 (publication date: Nov. 2011) (Abstract only).

Frequently Asked Questions About Medical Foods; Second Edition, Guidance for Industry, U.S. Department of Health and Human Services Food and Drug Administration Center for Food Safety and Applied Nutrition May 2016.

Miller et al., "Guinea Pig Epidermis Generates Putative Anti-Inflammatory Metabolites from Fish Oil Polyunsaturated Fatty Acids," Lipids, 24(12):998-1003 (publication date: 1989).

Ziboh et al., "Metabolism of polyunsaturated fatty acids by skin epidermal enzymes: generation of antiinflammatory and antiproliferative metabolites 1-3," Am J Clin Nutr 71(1 Suppl:361S-6S) (publication date: Jan. 2000).

\* cited by examiner

OILS WITH ANTI-INFLAMMATORY ACTIVITY CONTAINING NATURAL SPECIALIZED PRORESOLVING MEDIATORS AND THEIR PRECURSORS

This application is a continuation of U.S. patent application Ser. No. 16/297,240 (now U.S. Pat. No. 11,077,083) filed on Mar. 8, 2019, which is a continuation of U.S. patent application Ser. No. 15/935,913 filed on Mar. 26, 2018, which is a continuation of U.S. patent application Ser. No. 14/400,198, filed on Nov. 10, 2014 (now U.S. Pat. No. 10,568,858), which is a 35 USC § 371 U.S. National Stage Application of International Patent Application No. PCT/US2013/040314, filed on May 9, 2013, entitled, "OILS WITH ANTI-INFLAMMATORY ACTIVITY CONTAINING NATURAL SPECIALIZED PRORESOLVING MEDIATORS AND THEIR PRECURSORS," which claims priority to U.S. Provisional Patent Application No. 61/645,281, filed on May 10, 2012, the entire contents of each of which are incorporated herein by reference and relied upon.

FIELD OF THE INVENTION

The invention relates generally to the fields of natural products, inflammation, pathology, and medicine. More particularly, the invention relates to Specialized Proresolving Mediators (SPMs) and SPM precursors obtained from natural sources, and their use in nutritional supplements and pharmaceutical and cosmetic formulations for ameliorating inflammation and diseases having an inflammatory component.

BACKGROUND OF THE INVENTION

Inflammation is a complex biological response that animals make in attempt to remove or neutralize pathogens, irritants, or cell damage, and to initiate healing of injured tissues. The classical physical symptoms of inflammation include dolor (pain), calor (heat), rubor (redness), tumor (swelling), and functio laesa (loss of function). Initiation of an inflammatory response is associated with the activation of polymorphonuclear leukocytes (neutrophils), monocytes, and tissue macrophages. Activation of these cells unleashes a cascade of pro-inflammatory signaling events mediated by various small molecules and peptides, including prostaglandins, leukotrienes, chemokines and cytokines, and activated complement factors. These signaling events stimulate cellular chemotaxis, endothelial permeability, vasodilation, stimulation of sensory nerves, and activation of coagulation, which in turn lead to the physical symptoms of inflammation. Of importance, it is now understood that also the termination of inflammation, resolution, is an actively regulated part of the inflammatory response which involves a coordinated set of cellular and molecular events in order to restore tissue structure and function.

While inflammation is beneficial and indeed required for good health, it can also go awry and cause disease. For example, reperfusion injury following ischemia (e.g., in myocardial infarction or ischemic stroke) stimulates an acute inflammatory response that can damage tissue. And when a normal inflammatory response fails to terminate (resolve) alter removal of the original stimulus, chronic inflammation can ensue. Chronic inflammation damages healthy tissue and can cause or aggravate a number of different diseases including, e.g., atherosclerosis and other diseases of the vascular system, asthma, acne, psoriasis, rheumatoid arthritis, chronic obstructive pulmonary disease, cystic fibrosis, inflammatory bowel disease, and different kinds of autoimmune disease. Chronic inflammation has also been associated with type-2 diabetes, obesity, Alzheimer's disease, and cancer.

The resolution of inflammation is now recognized to constitute an active physiological process that forms an integral part of the inflammatory response. Resolution as the disappearance of the inflammatory exudate, and restoration of proper tissue structure and function, is mediated by several different molecular and cellular mechanisms. These include the clearance and metabolic destruction of inflammatory cytokines; formation of anti-inflammatory mediators such as transforming growth factor-beta, interleukin-10, annexin A1, and lipoxin A4; apoptosis of pro-inflammatory neutrophils; active recruitment of immunoregulatory monocytes/macrophages and eosinophils; and efferocytosis and egress of inflammatory leukocytes. Of particular relevance, it has been discovered that a family of substances collectively named Specialized Proresolving Mediators (SPMs) are central regulators of resolution. SPMs have potent anti-inflammatory activities (namely they reduce neutrophil infiltration), actively stimulate the removal and disappearance of the inflammatory exudate, expedite clearance of infection, and stimulate wound healing. SPMs are a genus of recently characterized lipid mediators identified in resolving exudates of inflammatory lesions, and comprise enzymatically oxygenated derivatives of long chain polyunsaturated fatty acids such the omega-3 polyunsaturated fatty acids ($\omega$-3 PUFA) eicosapentaenoic acid (EPA) and docosahexaenoic acid (DHA). SPMs have potent agonistic activities on specific G protein-coupled receptors, thereby activating different aspects of the resolution of inflammation. The SPMs consist of several different families of long chain $\omega$-3 PUFA-derived lipid mediators: resolvins, protectins and maresins—members of each of which control the duration and magnitude of inflammation by stimulating endogenous resolution mechanisms (Bannenberg & Serhan, 2010).

The biosynthesis of SPMs involves the positional and stereospecific incorporation of one or two molecules of molecular oxygen into a polyunsaturated fatty acid, catalyzed by substrate- and positionally-selective fatty acid oxygenases such as lipoxygenases, cyclooxygenase type-2 when acetylated by aspirin, and several cytochrome P450 oxidases. The PUFA which are currently best understood to act as substrate for the formation of SPMs are EPA and DHA.

The first step in the endogenous formation of SPMs involves the enzymatic oxygenation of a long chain $\omega$-3 PUFA in a stereochemically-defined manner leading to the formation of specific fatty acid hydroperoxides. The fatty acid hydroperoxides can be transformed to SPMs via several biosynthetic routes. The first is a reduction of the hydroperoxyl group to form the corresponding monohydroxylated fatty acid. Some of these monohydroxylated products function as intermediate precursors for a subsequent enzymatic oxygenation to form dihydroxylated and trihydroxylated SPMs. For example, 17-hydroxy-docosahexaenoic acid (17-HDHA), the product of a 15-lipoxygenase-catalyzed oxygenation with DHA, is the substrate for the formation of four distinct trihydroxylated resolvins RvD1, RvD2, RvD3, and RvD4. In this manner, 17-HDHA can be considered an SPM precursor. In a different biosynthetic pathway, the first formed fatty acid hydroperoxide can rearrange enzymatically to form an epoxide and is thereafter hydrolyzed enzymatically, to form a dihydroxylated product. Examples of such dihydroxylated lipid mediators are protectin D1 and maresin 1.

EPA and DHA thus constitute endogenous substrates in the bodies of animals and humans from which the in vivo formation proceeds to form EPA- and DHA-derived resolvins (so called E-series and D-series resolvins, respectively), and DHA-derived protectins and maresins, which are dihydroxylated and trihydroxylated EPA and DHA derivatives with potent anti-inflammatory and resolution-activating activity in vivo (Bannenberg and Serhan, 2010). The resolvins, protectins, and maresins are SPMs and act as endogenous receptor ligands or allosteric modulators to potently activate cellular responses that concertedly activate anti-inflammatory actions and expedite, stimulate, and trigger the resolution of inflammation. Furthermore, several enzymatically formed epoxide derivatives of EPA and DHA are now also known to possess potent anti-inflammatory activity themselves as well (Wagner, 2011) and are considered as SPMs here. Prior literature has also described the presence of several PUFA-derived lipid mediators in their free carboxylic acid form in cells and tissue of trout and anchovy (Pettitt, 1989; Hong, 2005; Oh, 2011; Raatz, 2011). The formation of SPMs occurs endogenously within the bodies of organisms, in several tissues and cell types, and occurs intracellularly. The substrate for SPM formation are the free carboxylic acid forms of EPA and DHA; these free fatty acids have been liberated by a phospholipase from membrane phospholipids containing EPA and DHA. There is no prior description that SPMs which are naturally formed within the cells or tissues of living organisms can be found outside the body of an animal or human being.

Several SPMs have now been synthesized by chemical synthesis methods. The synthetic SPMs have been instrumental in the delineation of the chemical structures and activity of the SPMs formed by cells in the bodies of animals. Also, structural analogues of SPMs have been synthesized by chemical synthesis methods. The advantage of synthetic forms of SPMs is their well-controlled purity. However, chemical synthesis of SPMs is a technically challenging and expensive process, since it is difficult to obtain the precise stereochemistry and double bond geometries that are important for bioactivity. It is therefore of high interest to have access to and obtain large quantities of the naturally bioactive forms of the SPMs.

Of particular relevance to the current invention, some of the monohydroxylated and epoxygenated derivatives constitute biosynthetic intermediates with more potent anti-inflammatory activity than EPA and DHA since they are more proximate intermediates in the biosynthesis of several SPMs than EPA and DHA themselves. These intermediate precursors are therefore considered SPM precursors.

It is of interest to note that several other long chain omega-3 PUFA, such as docosapentaenoic acid (ω-3), can also be transformed into oxygenated derivatives by the same oxygenases, with some derivatives having marked anti-inflammatory activity. There are also long chain omega-6 PUFA-derived anti-inflammatory and resolution-stimulating (proresolving) lipid mediators, such as lipoxin A4 formed through two enzymatic oxygenation steps from arachidonic acid, prostaglandin D2 formed from arachidonic acid by cyclooxygenases which gives rise to dehydration products with potent anti-inflammatory activity, and lipid mediators derived from docosapentaenoic acid (ω-6) with anti-inflammatory activities. In this respect it is important to understand that also arachidonic acid is an essential long chain PUFA, like EPA and DHA, and is usually present in all organisms that also contain long chain ω-3 fatty acids.

Even though the chemical structures of several SPMs are now known and their anti-inflammatory and pro-resolving activities have been studied in some detail in different experimental models of inflammation, no nutritional supplement, cosmetical formulation, or approved pharmaceutical formulation that contains an SPM has been developed for the inhibition or resolution of inflammation.

Because increased blood levels of EPA and DHA are associated with decreased incidence of, and propensity to develop, cardiovascular disease, the oral supplementation of omega-3 PUFA-containing oils is increasingly being used to ameliorate inflammation with some degree of success. The anti-inflammatory potential of dietary long chain ω-3 PUFA is widely believed to be related to the increase in tissue levels of EPA and DHA. Augmenting endogenous levels of EPA and DHA is commonly believed to favor an anti-inflammatory status through competition for the endogenous formation of the inflammation-activating eicosanoids derived from the omega-6 PUFA arachidonic acid (AA), the formation of EPA and DHA-derived 3-series prostaglandins and thromboxane with much lower inflammatory potency and efficacy, and biophysical changes within membrane domains and membrane proteins which modulate immune cell function. However, recent research has shown that long chain ω-3 PUFA are serving as endogenous substrates for the enzymatic formation of endogenous SPMs which act as autacoids to functionally antagonize inflammation and which actively expedite resolution. This recent recognition that EPA and DHA act as the physiological substrate for the formation of autacoids which drive the resolution of inflammation, affords renewed understanding of the essential nature of long chain ω-3 PUFA for human health. It is now well established that increased consumption of EPA and DHA-containing foods increase the tissue levels of these ω-3 PUFA. More recently, it has been shown that dietary supplementation with EPA and DHA indeed permits a measurable increase in the endogenous formation of some EPA- and DHA-derived oxygenated lipid mediators in humans (Anta, 2005; Shearer, 2010; Mas, 2012).

Long chain polyunsaturated fatty acids containing an omega-3 double bond are naturally formed by algae and other microorganisms forming the basis of the biotrophic chain of transfer of long chain ω-3 fatty acids such as EPA and DHA (Gladyshev, 2013) Mammals depend on the adequate supply of EPA and especially DHA through dietary sources, mainly through consumption of fish containing significant tissue levels of EPA and DHA which have upon their turn obtained these essential PUFA from the food chain. Mammals including man can endogenously synthesize EPA and DHA from alpha-linolenic acid, however the efficiency of this conversion is very limited and not adequate for the requirements for EPA and DHA. Dietary intake of EPA- and DHA-containing foods, and dietary supplementation with oils containing significant levels of EPA and DHA, are currently viewed as appropriate means to obtain a daily intake that can significantly increase the levels of long chain ω-3 PUFA and thereby attain an increased capacity to lower the intensity and duration of inflammatory reactions and disease.

Dietary requirements vary with age and life stage, and the essential nature of EPA and DHA for human health is therefore conditional. Circumventing the dependence of the substantial human need for long chain ω-3 PUFA on the natural food chain and growing global human demands for long chain ω-3 PUFA sufficiency, recent progress in biotechnology has permitted the creation of e.g. transgenic plants and microorganisms endowed with the biosynthetic capacity to form long chain ω-3 PUFA such as EPA and DHA (Petrie, 2012).

Dietary supplementation with oils containing long chain ω-3 PUFA is currently achieved by consumption of formulations which encompass many different presentations. The oils currently employed consist for the largest part (in volumes consumed) of EPA- and DHA-containing oils extracted from fish, of which the Peruvian anchovy makes up a substantial part. Other oils include those extracted from e.g. salmon and tuna. There is available a variety of different grades of oils ranging from oils which have been cold-pressed and which have undergone very few steps to only clear the oil from color or odorous substances present in the oil, to oils which have been selectively concentrated towards obtaining a specific long chain ω-3 fatty acid. Fish oils containing modest concentrations of long chain ω-3 PUFA (usually up to approximately 30%), or with concentrations increased by distillation to approximately 55%, are used widely in nutritional supplements for the treatment of, for example, hypertriglyceridemia, and for vascular and eye health. One good example of a long chain ω-3 PUFA concentrate made from fish oil which can currently be produced at industrial scale for the pharmaceutical sector contains 97% EPA in the form of an ethyl ester.

General methods involving lipid chemistry, industrial processes relating to oils and fatty acids, and conventional pharmaceutical sciences, are described in: (Remington, 2005; Martinez, 2007; Gunstone & Padley, 1997; Shahidi, 2005).

The fish oil industry currently manufactures a range of different EPA- and DHA-containing oil grades. EPA and DHA-containing oils are also extracted from other organisms such as krill, squid, algae, yeasts, protozoa, and from transgenic plants endowed with genes coding for enzymes that permit the biosynthesis of EPA and DHA and other long chain ω-3 PUFA such as stearidonic acid (SDA). Formulations available on the market for human consumption range from oils as such, encapsulated oils, emulsions, and stabilized powders. In all cases, the objective is to provide dietary supplements and pharmaceutical ingredients which aim to provide sufficiently high doses to humans to aid in augmenting endogenous tissue levels of EPA and DHA. Although relatively rapid absorption and redistribution of EPA and DHA into specific cell types, platelets and lipoproteins in the circulation can be measured (within 24 hours), it is generally accepted that the health-promoting actions of EPA and DHA upon oral consumption need significant time due to the supposed requirement that increased tissue levels of EPA and DHA need to be build up and which takes several weeks to months of taking doses of at least several hundreds of milligrams of EPA and DHA every day.

A characteristic of the need to provide EPA and DHA as essential nutrients for lowering inflammatory reactions, and preventing and treating inflammatory conditions, is that the endogenous enzymatic conversion of EPA and DHA, attained by dietary food intake and specific supplementation, to SPMs is a multistep enzymatic process which involves the liberation of phospholipid-bound EPA and DHA by phospholipases, followed by one or more enzymatic oxygenation reactions catalyzed by specific fatty acid oxygenases to form the active SPMs. These processes function adequately under healthy conditions, however low EPA and DHA tissue levels, as well as limited or inadequate conversion in the tissues of the body of long chain polyunsaturated fatty acids to SPMs are considered to contribute to, predispose to, or underlie inflammatory conditions and exaggerated inflammatory reactions.

BRIEF DESCRIPTION OF THE INVENTION

The invention is based on the surprising discovery that Specialized Proresolving Mediators (SPMs) and SPM precursors are present in oils extracted from organisms containing long chain ω-3 PUFA. Oils containing at least one SPM or SPM precursor and having anti-inflammatory or resolution-stimulating (proresolving) activity can be produced using a method comprising the steps of measuring the presence or level of SPMs or SPM precursors in a long chain ω-3 PUFA-containing oil (such as a crude, refined, or concentrated long chain ω-3 fatty acid-containing oil), fractionating the oil into a plurality of fractions, measuring the anti-inflammatory or resolution-stimulating activity of the oil fractions, and optionally repeating these three steps, to obtain an oil that contains or is enriched with at least one SPM or SPM precursor and has anti-inflammatory or resolution-stimulating activity. The SPMs and SPM precursors can be found in the form of saponifiable substances. The oils can furthermore contain long chain ω-3 PUFA, such as EPA and DHA.

Technologies which can be employed for such fractionation include extraction and separation methods. Technologies that are of particular interest for obtaining oils containing or enriched with SPMs and SPM precursors are supercritical fluid extraction (SFE) and supercritical fluid chromatography (SFC) employing carbon dioxide as solvent. The administration to subjects of an effective amount of these oils constitutes a method of reducing inflammation or stimulating the resolution of inflammation. The oils can be used for the manufacturing of nutritional supplements, pharmaceutical formulations, and cosmetical formulations, comprising an effective amount of an oil with anti-inflammatory or resolution-stimulating activity. These supplements and formulations thus constitute anti-inflammatory and proresolving compositions that can be manufactured in large quantities and do not require the addition of expensive chemically-synthesized SPMs.

Although methods and materials similar or equivalent to those described herein can be used in the practice or testing of the present invention, suitable methods and materials are described below. All patents, patent applications, and publications mentioned herein are incorporated by reference in their entirety. In the case of conflict, the present specification, including definitions will control. In addition, the particular embodiments discussed below are illustrative only and not intended to be limiting. Other aspects of the present invention will be evident for a person skilled in the art in view of the description of the invention.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE INVENTION

Figure 1A:
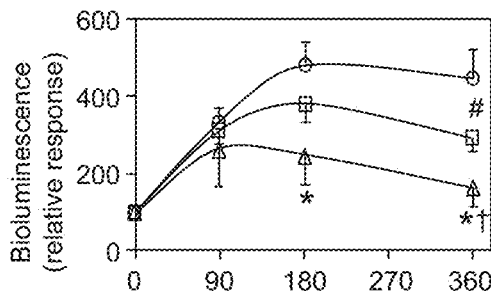
FIGS. 1A-1H shows the effect alter oral administration of a series of consecutively eluted oil fractions (number 1-8, respectively), obtained by industrial-scale SFC fractionation of an intermediate long chain ω-3 PUFA-ethyl ester concentrate (containing 70% EPA-ethyl ester (EE) and DHA-EE combined), on acute inflammatory changes occurring subcutaneously in mice induced by subcutaneous (s.c.) administration of lipopolysaccharide (LPS).
Figure 1B:
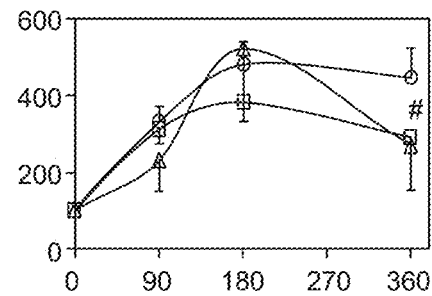
Figure 1C:
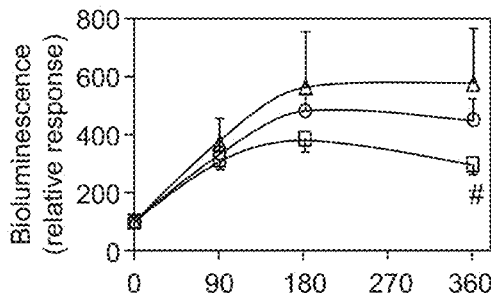
Figure 1D:
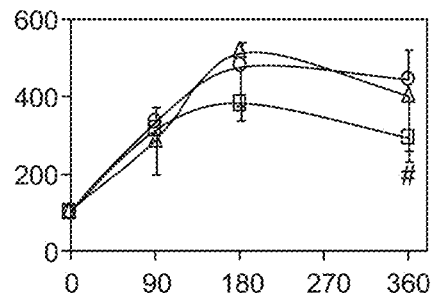
Figure 1E:
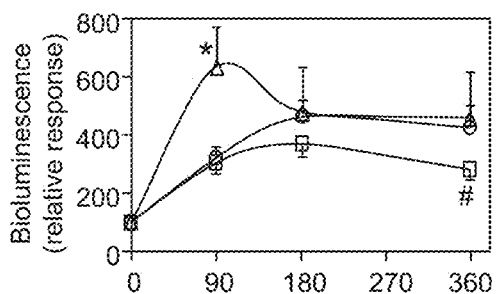
Figure 1F:
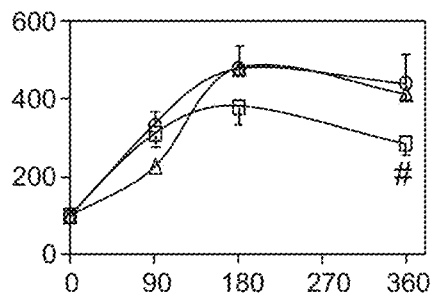
Figure 1G:
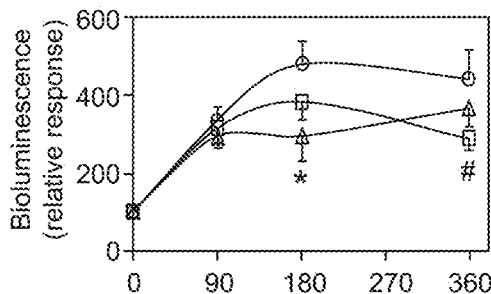
Figure 1H:
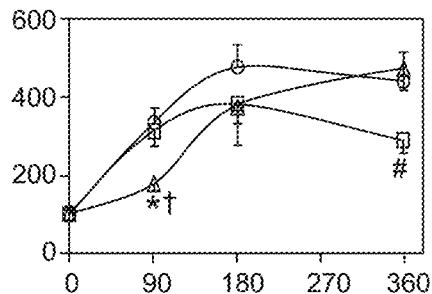

It has been discovered that SPMs and SPM precursors are contained in oils derived from natural sources including fish, crustaceae (krill), algae (long chain ω-3 PUFA-producing algae), mollusks, and from other organisms containing long chain ω-3 PUFA. This permits the production of oils with anti-inflammatory and resolution-stimulating activity purposefully containing or enriched with one or more Specialized Proresolving Mediators (SPMs) and SPM precursors from natural sources, as well as nutritional supplements, pharmaceutical formulations, and cosmetical formulations containing these oils, and methods of using such supplements and formulations to treat or prevent inflammatory conditions and diseases associated with inflammation, by inhibiting inflammation or stimulating the resolution of inflammation. The below described embodiments illustrate representative examples of these methods and compositions. Nonetheless, from the description of these embodiments, other aspects of the invention can be made and/or practiced based on the description provided below. Unless otherwise defined, all technical terms used herein have the same meaning as commonly understood by one of ordinary skill in the art to which this invention belongs.

A first aspect of the present invention is formed by oils that have anti-inflammatory or resolution-stimulating activity characterized in that they contain or are enriched with at least one SPM or SPM precursor, wherein the SPM or SPM precursor originates from an oil obtained from organisms containing long chain ω-3 fatty acids.

As used in the present invention, the term "enriched" refers to an oil containing Specialized Proresolving Mediators (SPMs) and/or SPM precursors when it contains a higher level of SPMs and/or SPM precursors than the source from which it was made.

As used in the present invention, the term "Specialized Proresolving Mediator (SPM)" relates to a PUFA-derived enzymatically-oxygenated derivative which has potent anti-inflammatory and resolution-activating activity and which acts as endogenous regulator of the inflammatory response to bring an inflamed tissue back towards its non-inflamed and healthy state. SPMs act as endogenous receptor ligands or allosteric modulators to potently activate cellular responses that concertedly activate anti-inflammatory actions and expedite, stimulate, and trigger resolution of inflammation.

As used in the present invention, the term "SPM precursor" refers to an enzymatically oxygenated derivative of a PUFA which requires an additional enzymatic reaction to convert it to a SPM. An SPM precursor is a more proximate substrate for the endogenous formation of an SPM than the corresponding PUFA substrate itself.

These oils contain or are enriched with at least one SPM or SPM precursor that originates from an oil extracted from organisms containing long chain ω-3 PUFA, preferably fish, crustaceae, algae, and mollusks, or other long chain ω-3 PUFA-containing organisms, such as other marine organisms, plants, microbial organisms, and transgenic organisms endowed with the capacity to form long chain ω-3 polyunsaturated fatty acids.

SPMs that may be present in oils extracted from natural sources include the following:

resolvin E1 (RvE1; 5 S,12R,18R-trihydroxy-eicosa-6Z,8E, 10E,14Z,16E-pentaenoic acid), 18 S-resolvin E1 (18S-RvE1; 5 S,12R,18S-trihydroxy-eicosa-6Z,8E,10E,14Z,16E-pentaenoic acid), 20-hydroxy-RvE 1 (5 S,12R,18R,20-tetrahydroxy-eicosa-6Z, 8E, 10E,14Z,16E-pentaenoic acid), resolvin E2 (RvE2; 5 S,18-dihydroxy-eicosa-6E,8Z,11Z, 14Z,16E-pentaenoic acid), resolvin E3 (RvE3; 17,18R-dihydroxy-eicosa-5Z,8Z,11Z, 13E,15E-pentaenoic acid), 18S-resolvin E3 (18S-RvE3; 17,18S-dihydroxy-eicosa-5Z, 8Z,11Z,13E,15E-pentaenoic acid), 17,18-epoxy-eicosa-5Z,8Z,11Z,13E,15E-pentaenoic acid, lipoxin $A_5$ (LXA$_5$; 5S,6R,15S-trihydroxy-eicosa-7E,9E, 11Z,13E,17Z-pentaenoic acid), 15-epi-lipoxin A$_5$ (LXA$_5$; 5S,6R,15R-trihydroxy-eicosa-7E,9E,11Z,13E,17Z-pentaenoic acid), maresin 1 (MaR1; 7R,14S-dihydroxy-docosa-4Z,8E,10E, 12Z,16Z,19Z-hexaenoic acid), 7S-maresin 1 (7S-MaR1; 7S,14S-dihydroxy-docosa-4Z,8E, 10E,12Z,16Z,19Z-hexaenoic acid), 7S,14S-diHDHA (7S,14S-dihydroxy-docosa-4Z,8E,10Z, 12E,16Z,19Z-hexaenoic acid), protectin D1 (PD1; 10R,17S-dihydroxy-docosa-4Z,7Z,11E, 13E,15Z,19Z-hexaenoic acid), 10S,17 S-diHDHA (10S,17S-dihydroxy-docosa-4Z,7Z,11E, 13Z,15E,19Z-hexaenoic acid), 14S,21S-diHDHA (14S,21S-dihydroxy-docosa-4Z,7Z,10Z, 12E,16Z,19Z-hexaenoic acid), 14S,21R-diHDHA (14S,21R-dihydroxy-docosa-4Z,7Z,10Z, 12E,16Z,19Z-hexaenoic acid), 14R,21S-diHDHA (14R,21S-dihydroxy-docosa-4Z,7Z,10Z, 12E,16Z,19Z-hexaenoic acid), 14R,21R-diHDHA (14R,21R-dihydroxy-docosa-4Z,7Z, 10Z,12E,16Z,19Z-hexaenoic acid), 13S,14 S-epoxy-DHA (13 S,14S-epoxy-docosa-4Z,7Z,9E, 11E,16Z,19Z-hexaenoic acid), 16,17 S-diHDHA (16,17S-dihydroxy-docosa-4Z,7Z,10Z, 12E,14E,19Z-hexaenoic acid), 16,17-epoxy-DHA (16,17-epoxy-docosa-4Z,7Z,10Z,12E,14E,19Z-hexaenoic acid), resolvin D1 (RvD1; 7S,8R,17 S-trihydroxy-docosa-4Z, 9E,11E,13Z,15E,19Z-hexaenoic acid), resolvin D2 (RvD2; 7S,16R,17S-trihydroxy-docosa-4Z,8E,
10Z,12E,14E,19Z-hexaenoic acid),
resolvin D3 (RvD3; 4S,11R,17S-trihydroxy-docosa-5Z,'7E,
9E,13Z,15E,19Z-hexaenoic acid),
resolvin D4 (RvD4; 4S,5,17S-trihydroxy-docosa-6E,8E,
10Z,13Z,15E,19Z-hexaenoic acid),
resolvin D5 (RvD5; 7S,17S-dihydroxy-docosa-5Z,8E,10Z,
13Z,15E,19Z-hexaenoic acid),
resolvin D6 (RvD6; 4S,17S-dihydroxy-docosa-5E,7Z,10Z,
14Z,16E,19Z-hexaenoic acid),
aspirin-triggered resolvin D1 (AT-RvD1; 7S,8R,17R-trihydroxy-docosa-4Z,9E,11E,13Z,15E, 19Z-hexaenoic acid),
aspirin-triggered resolvin D2 (AT-RvD2; 7S,16R,17R-trihydroxy-docosa 4Z,8E,10Z,
12E,14E,19Z-hexaenoic acid),
aspirin-triggered resolvin D3 (AT-RvD3; 4S,11,17R-trihydroxy-docosa-5Z,7E,9E,13Z,15E,19Z-hexaenoic acid),
aspirin-triggered resolvin D4 (AT-RvD4; 4S,5,17R-trihydroxy-docosa-6E,8E,10Z,
13Z,15E,19Z-hexaenoic acid),
aspirin-triggered resolvin D5 (AT-RvD5; 7S,17R-dihydroxy-docosa-5Z,8E,10Z,13Z,
15E,19Z-hexaenoic acid),
aspirin-triggered resolvin D6 (AT-RvD6; 4S,17R-dihydroxy-docosa-5E,7Z,10Z,14Z,
16E,19Z-hexaenoic acid),
7S,17S-diHDPA n–3 (7S,17S-dihydroxy-docosa-8E,10Z,
13Z,15Z,19Z-pentaenoic acid (ω-3)) lipoxin $A_4$ ($LXA_4$; 5S,6R,15S-trihydroxy-eicosa-7E,9E,11Z,13E-tetraenoic acid), 15-epi-lipoxin $A_4$ (15-epi-$LXA_4$; 5S,6R,15R-trihydroxy-eicosa-7E,9E,11Z,13E-tetraenoic acid),
delta12-prostaglandin $J_2$ (delta12-$PGJ_2$; 11-oxo-15S-hydroxy-prosta-5Z,9,12E-trienoic acid)
15-deoxy-delta12,14-prostaglandin $J_2$ (15-deoxy-delta12,14-$PGJ_2$; 11-oxo-prosta-5Z,9,12E,14E-tetraenoic acid)
11(12)-epoxy-eicosatetraenoic acid (11(12)-EpETE; 11(12)-epoxy-eicosa-5Z,8Z,14Z,17Z-tetraenoic acid)
17(18)-epoxy-eicosatetraenoic acid (17(18)-EpETE; 17(18)-epoxy-eicosa-5Z,8Z,11Z,14Z-tetraenoic acid)
19(20)-epoxy-docosapentaenoic acid (19(20)-EpDPE; 19(20)-epoxy-docosa-4Z,7Z,10Z,13Z,16Z-pentaenoic acid)
10S,17S-diHDPA n–6 (10S,17S-dihydroxy-docosa-4Z,7Z,11E,13Z,15E-pentaenoic acid),
7,17-diHDPA n–6 (7,17-dihydroxy-docosa-4Z,8E,10Z,13Z,15E-pentaenoic acid),
7,14-HDPA n–6 (7,14-dihydroxy-docosa-4Z,8E,10Z,12Z,16Z-pentaenoic acid),
10S,17S-HDPA n–6 (10S,17S-dihydroxy-docosa-7Z,11E,13Z,15E,19Z-pentaenoic acid), and
7,17-HDPA n–6 (7,17-dihydroxy-docosa-8E,10Z,13Z,15E,19Z-pentaenoic acid).

Precursors of SPMs that may be present or enriched in oils extracted from natural sources include the following. Examples of the presence of these compounds in oils and oil fractions are shown in Examples 1-3.

| | |
|---|---|
| 5S-HEPE | (5S-hydroxy-eicosa-6E,8Z,11Z,14Z,17Z-pentaenoic acid); |
| 11S-HEPE | (11S-hydroxy-eicosa-5Z,8Z,12E,14Z,17Z-pentaenoic acid); |
| 12S-HEPE | (12S-hydroxy-eicosa-5Z,8Z,10E,14Z,17Z-pentaenoic acid); |
| 12R-HEPE | (12R-hydroxy-eicosa-5Z,8Z,10E,14Z,17Z-pentaenoic acid); |
| 15S-HEPE | (15S-hydroxy-eicosa-5Z,8Z,11Z,13E,17Z-pentaenoic acid); |
| 18S-HEPE | (18S-hydroxy-eicosa-5Z,8Z,11Z,14Z,16E-pentaenoic acid); |
| 18R-HEPE | (18R-hydroxy-eicosa-5Z,8Z,11Z,14Z,16E-pentaenoic acid); |
| 4S-HDHA | (4S-hydroxy-docosa-5E,7Z,10Z,13Z,16Z,19Z-hexaenoic acid); |
| 7S-HDHA | (7S-hydroxy-docosa-4Z,8E,10Z,13Z,16Z,19Z-hexaenoic acid); |
| 10S-HDHA | (10S-hydroxy-docosa-4Z,7Z,11E,13Z,16Z,19Z-hexaenoic acid); |
| 11S-HDHA | (11S-hydroxy-docosa-4Z,7Z,9E,13Z,16Z,19Z-hexaenoic acid); |
| 14S-HDHA | (14S-hydroxy-docosa-4Z,7Z,10Z,12E,16Z,19Z-hexaenoic acid); |
| 14R-HDHA | (14R-hydroxy-docosa-4Z,7Z,10Z,12E,16Z,19Z-hexaenoic acid); |
| 17S-HDHA | (17S-hydroxy-docosa-4Z,7Z,10Z,13Z,15E,19Z-hexaenoic acid); |
| 17R-HDHA | (17R-hydroxy-docosa-4Z,7Z,10Z,13Z,15E,19Z-hexaenoic acid); |
| 20S-HDHA | (20S-hydroxy-docosa-4Z,7Z,10Z,13Z,16Z,19Z-hexaenoic acid); |
| 17S-HDPAn-6 | (17S-hydroxy-docosa-4Z,7Z,10Z,13Z,15E-pentaenoic acid); |
| 14S-HDPAn-6 | (14S-hydroxy-docosa-4Z,7Z,10Z,12E,16Z-pentaenoic acid); |
| 10S-HDPAn-6 | (10S-hydroxy-docosa-4Z,7Z,11E,13Z,16Z-pentaenoic acid); |
| 17S-HDPAn-3 | (17S-hydroxy-docosa-7Z,10Z,13Z,15E,19Z-pentaenoic acid); |
| 14S-HDPAn-3 | (17S-hydroxy-docosa-7Z,10Z,12E,16Z,19Z-pentaenoic acid); |
| 10S-HDPAn-6 | (10S-hydroxy-docosa-7Z,11E,13Z,16Z,19Z-pentaenoic acid); |
| 15S-HETE | (15S-hydroxy-eicosa-5Z,8Z,11Z,13E-tetraenoic acid); and/or |
| 15R-HETE | (15R-hydroxy-eicosa-5Z,8Z,11Z,13E-tetraenoic acid). |

In addition to the foregoing, SPMs and SPM precursors derived from any of the following omega-3 PUFA or omega-6 PUFA may be present or enriched in oils extracted from natural sources. These fatty acids may give rise to SPM precursors and SPMs through enzymatic oxygenation.

TABLE 1

| Fatty acid name | Chemical name |
|---|---|
| Hexadecatrienoic acid (HTA) | 16:3 (n-3) all-cis-7,10,13-hexadecatrienoic acid |
| a-Linolenic acid (ALA) | 18:3 (n-3) all-cis-9,12,15-octadecatrienoic acid |
| Stearidonic acid (SDA) | 18:4 (n-3) all-cis-6,9,12,15-octadecatetraenoic acid |
| Nonadecatetraenoic acid | 19:4 (n-3) all-cis-7,10,13,16-nonadecatetraenoic acid |
| Eicosatrienoic acid | 20:3 (n-3) all-cis-11,14,17-eicosatrienoic acid |
| Eicosatetraenoic acid | 20:4 (n-3) all-cis-8,11,14,17-eicosatetraenoic acid |

TABLE 1-continued

| Fatty acid name | Chemical name |
| --- | --- |
| Eicosapentaenoic acid (EPA) | 20:5 (n-3) all-cis-5,8,11,14,17-eicosapentaenoic acid |
| Heneicosapentaenoic acid | 21:5 (n-3) all-cis-6,9,12,15,18-heneicosapentaenoic acid |
| Docosapentaenoic acid (DPA) | 22:5 (n-3) all-cis-7,10,13,16,19-docosapentaenoic acid |
| Docosahexaenoic acid (DHA) | 22:6 (n-3) all-cis-4,7,10,13,16,19-docosahexaenoic acid |
| Tetracosapentaenoic acid | 24:5 (n-3) all-cis-9,12,15,18,21-tetracosapentaenoic acid |
| Tetracosahexaenoic acid | 24:6 (n-3) all-cis-6,9,12,15,18,21-tetracosahexaenoic |

In addition to the listed examples of SPMs and SPM precursors, it can be envisioned that other mono-, di-, and tri-hydroxylated and epoxygenated derivatives of the above mentioned polyunsaturated fatty acids may possess anti-inflammatory and proresolving activities and can be found to be present and enriched in oils obtained from organism which contain long chain ω-3 PUFA including fish, crustaceae, algae, mollusks, and marine organisms, plants, microbial organisms, as well as transgenic organisms endowed with the enzymatic capacity to form long chain ω-3 PUFA. Likewise, additional precursors of known SPMs and novel SPMs may be identified and enriched in such oils. In addition, the SPMs and SPM precursors may be present as esters and amides. The esters can be natural esters such as triglycerides, diglycerides, monoglycerides, and phospholipids, as well as esters prepared during the industrial processes commonly employed in the fish oil industry permitting the concentration of EPA and DHA from crude and refined fish oils, in particular the form of ethyl esters.

Any SPM, SPM precursor, or mixtures of SPMs and SPM precursors that are found in oils obtained from long chain ω-3 PUFA-containing organisms can be enriched or concentrated employing extraction and separation methods, for example, distillation technologies, and chromatographic fractionation and separation technologies.

The present invention has discovered that, and unanticipated to the known state of the art, SPMs and SPM precursors can be found as saponifiable substances in crude oils, in subsequently derived refined oils, and in oils in which the levels of long chain ω-3 PUFA, such as EPA and DHA, have been concentrated in the form of ethyl esters. For example, it is shown in Example 2 (FIG. 5A) that a widely employed crude oil extracted from anchovy, which is considered a good starting material for the omega-3 industry since it is relatively rich in EPA and DHA, contains the D-series resolvins RvD1 and RvD2 (both in acylated form). The saponifiable form of the SPMs or SPM precursors can also be present as ethyl esters as a result of the transesterification of long chain ω-3 PUFA-containing oils with ethanol to obtain fatty acid-ethyl ester oils that can be concentrated and fractionated employing specific distillation, extraction and chromatographic industrial procedures employed for ω-3 PUFA-ethyl ester concentration and purification. For example, many monohydroxylated lipid mediators which can function as SPM precursors are found in saponifiable form in the ethyl esterified omega-3 concentrates manufactured from anchovy oil, tuna liver oil, and in ethyl ester omega-3 concentrate manufactured from a mixture of mollusks and fish (FIGS. 2, 3A, FIGS. 3B, 5C, 6A, and 6B). The presence of the esterified forms of SPM precursors and SPMs themselves present in ethyl ester concentrates of long chain ω-3 PUFA oils demonstrates that these SPM precursors and SPMs were originally present in acylated form in the crude marine oils and organisms from which the crude oil was extracted. In the process of transesterification of a refined oil with ethanol, these acylated SPM precursors and SPMs also become transesterified to the corresponding ethyl esters. This finding is of highly significant and unanticipated nature, since SPMs and SPM precursors are not known to be found in acylated form in the cells and tissues of organisms which are used for the preparation of ω-3 PUFA-containing oils manufactured for use as e.g. nutritional supplements and pharmaceutical ingredients. This aspect of the invention does not exclude the presence or enrichment in long chain ω-3 PUFA-containing oils of SPMs and SPM precursors as free carboxylic acids, which are the chemical form of SPMs and SPM precursors previously described in the literature to be formed within cells and organisms from long chain ω-3 PUFA substrates. In addition, the oils containing SPMs or SPM precursors can contain long chain ω-3 PUFA, such as EPA and DHA.

Another aspect of the invention is a method for the production of oils with anti-inflammatory or resolution-stimulating activity and containing measurable levels of SPMs and/or SPM precursors. The method includes the following steps; i) measuring the presence or concentration of SPMs or SPM precursors in a long chain ω-3 PUFA-containing oil. This can be e.g. a crude, refined, or concentrated long chain ω-3 PUFA-containing oil; ii) fractionating the oil into a plurality of fractions; iii) measuring the anti-inflammatory or resolution-stimulating activity of the fractions; iv) and, optionally, repeating the three steps, in order to obtain an oil with anti-inflammatory or resolution-stimulating activity, and containing or enriched with at least one SPM or SPM precursor.

Measuring the presence of SPMs and SPM precursors in an oil permits assessing or gauging the suitability of an oil to be fractionated in order to obtain an oil which contains at least one SPM or SPM precursor, has a desirable combination of SPMs and SPM precursors, or which has an enrichment with at least one SPM or SPM precursor. The presence and absolute levels of SPMs and SPM precursors in a given sample or fraction can be determined by analytical chemistry techniques such as liquid chromatography coupled to electrospray ionization tandem mass spectrometry (LC/ESI-MS/MS), and gas chromatography/mass spectrometry (GC/MS) (Yang, 2011). Other techniques for detecting and/or quantifying SPMs and SPM precursors that might be used include immunoassays such as the Resolvin D1 ELISA assay marketed by Cayman Chemical Company (Ann Arbor, Mich.), and Neogen Corporation's LXA4 and AT-LXA4 assay kits.

Fractionating a crude, refined, or concentrated long chain ω-3 PUFA-containing oil into a plurality of fractions, permits the production of oils which contain higher concentrations of the at least one SPM or SPM precursor than other fractions, or contain a desired combination of SPMs or SPM precursors. The fractionation of oils can be achieved with separation and extraction methods. Because the SPMs and/or SPM precursors present in the oils from natural sources will differ according to the natural source from which the crude oil was obtained, different methodologies will lead to various compositions of SPMs and SPM precursors in the various oils employed for finished product preparation.

Several extraction and separation technologies are available to obtain oils containing or enriched in at least one SPM or SPM precursor. Such technologies can operate on the molecular form in which the SPMs and/or SPM precursors were isolated, such as triglycerides in fish and vegetable oils, or phospholipids and triglycerides present in krill oils, or after transformation into a different chemical form, notably fatty acid ethyl esters. Oils composed of fatty acid ethyl esters can subsequently be employed to manufacture remodeled triglycerides or compositions containing high levels of free fatty acids. Oils containing SPMs and/or SPM precursors can be obtained from the here mentioned long chain ω-3 PUFA-containing crude oils as starting materials by one or a combination of several technologies. Suitable methodologies will be explained hereafter.

The extraction process involves heating the raw material containing long chain ω-3 PUFA (e.g., fish, krill, squid, or algae) to temperatures up to 95° C. The heat treatment step yields a "pre-pressing" liquid containing both water and fat. Subsequent pressing (of the left-over solid material obtained in the thermal treatment) at pressures of 130 to 170 bar and concomitant pressing with a screw-press yields a pressing liquid. The pre-pressing liquid and pressing liquid can be combined ("press water") and then fed into a 2-phase decanter to remove solids and obtain clarified "press water." The press-water is "de-oiled" by centrifugation in a separator, yielding a turbid oil. The turbid oil can then be "polished" by means of an additional centrifugation step with a separator to obtain a "crude" oil. An alternative process employs a two-phase decanter instead of a screw-press which simplifies the process by directly separating solid from oil-containing fluid, from which the oil is separated by an oil separator (polishing). In a third process, a decanter is used to separate heat-coagulated raw material directly into solid, water, and oil. The oil can then be polished with a separator to remove traces of water. Temperatures during separation processes are maintained between 95° C. and 98° C. Preferably, the application of heat is limited to the shortest time required to separate fat from heat-coagulated protein and water. Most of the SPMs and/or SPM precursors in the crude oil obtained by any of these extraction methods are in acylated form as esters within glycerides and phospholipids, and as amides.

A crude oil can be cleaned by a chemical "refining" process. This step involves washing the oil with alkaline and acid solutions in order to neutralize the oil, separation with a separator to remove the aqueous wash from the oil, hot water washing, a "bleaching" treatment of the oil with diatomaceous earths, activated carbon or silica, followed by filtering in order to remove (such as colored carotenoids, metals, contaminants) impurities by adsorption, and vacuum drying. Generally, temperatures between 95° C. and 98° C. are maintained during refining processes. An additional deodorization step can be applied which involves heating the oil up to 200° C. to remove volatile substances.

Alternatively, cold extraction techniques might be used to obtain oils that contain SPMs and/or SPM precursors.

Winterization of an oil is a process by which the oil is cooled at a controlled rate permitting the differential crystallization of distinct lipids based on differences in melting points—permitting separation of different lipid classes. This separation technique may be useful in the separation of waxes and lipids rich in saturated fatty acids from a lipid (usually triglyceride) fraction containing a higher content in SPMs and/or SPM precursors or acylated forms thereof.

One or more molecular distillation techniques might also be used for this purpose. Molecular distillation methods include thin film distillation, wiped film distillation, and short path distillation. In thin film evaporation and distillation, a film of the oil is created by rotating fans or rollers within a closed vessel. By the combined application of low pressure conditions and heating, the differential evaporation of distinct lipid components is achieved, permitting the relative enrichment of a lipid fraction of interest (i.e., those fractions containing higher levels of SPMs and/or SPM precursors). In wiped-film distillation the oil is actively wiped into a film onto a heated surface by a rotating barrel.

Short path evaporation distillation is a molecular distillation technique which is particularly useful for fractionation of compounds sensitive to oxidation by air through the introduction of an internal condenser within the vessel where evaporation or distillation is taking place. Like with thin film evaporation and distillation the fractionation is carried out under reduced pressure and heating. Pressure losses are diminished in this configuration and lower or shorter heating times may be achieved by this technique. A short path distillation plant comprises a supply tank, an evaporator, a vacuum pump, a degasser, rollers, heat exchangers, a condenser, a thermal conditioned tank and a continuous and closed circuit.

Molecular distillation steps can be performed in sequential order to concentrate a range of structurally similar fatty acids from an oil to obtain an oil fraction of interest. Another technique complementary to molecular distillation is vacuum rectification, which incorporates an external reflux process permitting higher levels of concentration at the inconvenience of higher contact times. Fatty acids in oils can be further concentrated by means of a selective precipitation step through the addition of urea, which selectively complexes saturated and monounsaturated fatty acids. Additional concentration technologies encompass ionic exchange employing cation- and anion-exchanging resins. Another technology which can permit selective concentration based on molecular size and weight is ultrafiltration.

An extraction technology which is of particular usefulness for the extraction of SPMs and SPM precursors is supercritical fluid extraction (SFE). A supercritical fluid extraction plant comprises a supply tank, pumps, a solvent tank, a continuous and closed circuit, an extraction column, atmospheric tanks and separators. By attaining specific combination of pressure and temperature the mobile phase can be brought above its supercritical point. SFE is commonly employed under countercurrent conditions whereby a steady state is achieved permitting selective enrichment of a component eluting from the top or bottom of the extraction column. SFE permits selective enrichment. SFE thus permits manufacturing of oils which are suitable starting material for subsequent separation technologies employed for selectively separating and purifying individual fatty acids, for example as their corresponding ethyl ester, permitting concentration up to levels that can approach near purity.

Chromatographic techniques are useful for achieving significant levels of separation of individual ethyl-esterified fatty acids, and are suitable for obtaining oils which are selectively enriched with SPMs and SPM precursors. These include conventional chromatography by high-pressure operation, moving-belt chromatography, counter-current chromatography, and supercritical fluid chromatography (SFC). A high-pressure chromatography employs mixtures of aqueous and organic solvents pumped at elevated pressure through a column containing a stationary phase. The stationary phase can have different polarities and particles size and geometries. By choosing optimal combinations of mobile phase, stationary phase, temperature acceptable separation of fatty acid-ethyl esters can be achieved.

Supercritical fluid chromatography (SFC) employs supercritical fluid (usually carbon dioxide) as a solvent and mobile phase. By careful modulation of the supercritical fluid density through pressure and temperature, eluting conditions can be optimized for the separation of individual lipids within a sample. The advantage of this technique is the employment of near ambient temperatures and the exclusion of oxygen during the chromatographic procedure to eliminate the risk for inadvertent oxidation. Installations encompass a supply vessel, pumps, a mobile phase tank, a continuous and closed circuit, a chromatography column, atmospheric tanks and separators. SFC permits chromatographic separation of fatty acid-ethyl esters. The mobile phase, since it is a gas at ambient pressure and temperature, is easily removed from the final oil fraction.

Preferred techniques for obtaining SPMs and/or SPM precursor-containing oils by fractionation of long chain ω-3 PUFA-containing oils are supercritical fluid extraction (SFE) and supercritical fluid chromatography (SFC). These techniques may be complemented optionally by one or more additional fractionation steps allowing enrichment of one or more defined SPMs and/or SPM precursors. Examples are described below. The following ranges of SFE and SFC conditions can be employed: temperature range between 27-60° C., pressure range between 80-180 bar, with silica, modified silica, reversed phase, chiral and argentated stationary phases, and solvent/feed ratios of 10-800 (Kg/Kg).

The combination of SFE and SFC permits enrichment of one or several specific SPMs and/or SPM precursors. The capacity to separate SPMs and/or SPM precursors furthermore permits recombining specific oil fractions in order to obtain a versatile range of ratios and combinations.

Additional chromatographic steps can be performed employing very specialized enrichment technologies such as chiral separations, and metal-affinity chromatography such as argentation chromatography with immobilized silver salts.

As a result of the technology employed for the preparation of the oils containing or enriched for SPMs and/or SPM precursors, the chemical forms of these molecules is commonly one of the following; ethyl esters when present in omega-3 concentrates, acylated within glycerides and phospholipids typical for crude and refined oils, or found as free carboxylic acids dissolved within the oils. Other chemical forms of the SPMs and SPM precursors may be found in crude and refined oils, such as amides. In a further embodiment, the SPMs and SPM precursor molecules can be further transformed according to known methods. For example, SPM-ethyl ester-containing oils can be transesterified again (either chemically or enzymatically) with a triglyceride or phospholipid to form a remodeled triglyceride or phospholipid, respectively. Esterified SPMs and SPM precursors can also be hydrolyzed to obtain the corresponding free fatty acid form, as a salt or the conjugate acid.

In a particular embodiment this invention furthermore may ultimately permit naturally-occurring SPMs and/or SPM precursors to be purified to homogeneity or near homogeneity (e.g., more than 80, 90, 95, 96, 97, 98, or 99% pure by weight).

Furthermore, crude oils originating from the same or from different organisms containing long chain ω-3 PUFA can be combined and used as starting material for subsequent enrichment procedures to obtain SPMs and SPM precursor-containing oils.

Determination of the anti-inflammatory or resolution-stimulating activity of the fractions containing higher concentrations of the at least one SPM or SPM precursor than other fractions, or containing a desired combination of SPM or SPM precursors, will establish the usefulness of the oil to make a therapeutic anti-inflammatory or resolution-stimulating composition. This can be preferably performed in vivo, in experimental models of inflammation that permit assessment of anti-inflammatory efficacy and potency, or measuring the resolution-activating activity of the oil fraction (Bannenberg, 2005). In vitro and cellular models may be employed for this purpose in order to measure a particular cellular or molecular aspect of anti-inflammatory or proresolving activities on the in vivo inflammatory response.

Another aspect of the invention is that the purposefully manufacturing of SPM- and SPM-precursor-containing or -enriched oils with anti-inflammatory and resolution-enhancing activities, can be used for reducing inflammation or stimulating the resolution of inflammation in a subject, the method comprising the step of administering an effective amount of an oil. The oils can be used for treating inflammation or diseases associated with inflammation, or preventing inflammation or diseases associated with inflammation. Fractionation of oils permits obtaining oils with specific anti-inflammatory or resolution-stimulating activity. A functional differentiation can be achieved by fractionation, with some oil fractions having anti-inflammatory activity and/or resolution-stimulating (proresolving) activity, other oil fractions having no significant anti-inflammatory activity, and/or even oil fractions may be obtained having an inflammation-promoting activity. Specific oils obtained through fractionation thus have the capability to modulate the inflammatory response distinctly.

Specific oils and oil fractions containing natural SPMs, SPM precursors, or mixtures of SPMs and/or SPM precursors can be particularly well suited to treat or prevent a specific inflammatory condition. For example, an oil containing or enriched with a particular SPMs and/or SPM precursors, or combination of more than one SPM or SPM precursor, might be selected for treating rheumatoid arthritis, based on research showing that these particular molecules are more beneficial for treating rheumatoid arthritis than either currently used ω-3 PUFA-containing oils, or other SPMs, SPM precursors, or mixtures of SPMs and/or SPM precursors, or known anti-inflammatory drugs. Other SPMs and/or SPM precursor-containing oils might be selected for making a composition for treating a different inflammatory condition, e.g., asthma, based on research. This method includes the step of administering to the subject an effective amount of an oil containing or enriched for at least one SPM or SPM precursor and having anti-inflammatory or resolution-stimulating activity.

The SPMs and/or SPM precursor-containing oils might further comprise a carrier or an excipient.

As used in the present invention, the terms "subject" or "patient" refers to animals, including mammals, preferably humans.

As used in the present invention, the terms "administer", "administering" or "administration", as used herein, refer to directly administering an oil or oil-containing composition to a subject or patient, which will deliver an effective amount of the active compound or substance to the subject's or patient's body.

As used in the present invention, the term an "effective amount" or "an amount effective to" means an amount adequate to cure or at least partially ameliorate the symptoms of a condition, disease or its complications.

Another aspect of the invention encompasses the anti-inflammatory or resolution-stimulating oils containing SPMs or SPM precursors in that these oils also contain long chain ω-3 PUFA. These can be EPA, and DHA, but also other long chain ω-3 PUFA such as stearidonic acid or docosapentaenoic acid.

Another aspect of the invention relates to the making of nutritional supplements, pharmaceutical formulations, and cosmetic formulations comprising an effective amount of SPM- and SPM-precursor-containing or -enriched oils with anti-inflammatory or resolution-enhancing activity obtained from organisms containing long chain ω-3 PUFA. After obtaining an oil or oil fraction which contains or is enriched for one or more naturally present SPMs and/or SPM precursors and that has anti-inflammatory or resolution-stimulating activity, the oil can be used to make a nutritional supplement, a pharmaceutical formulation, or a cosmetic formulation.

As used in the present invention, the term "Pharmaceutically acceptable" refers to those compounds, materials, compositions, supplements, formulations, and/or dosage forms which are, within the scope of sound medical judgment, suitable for contact with the tissues of human beings and animals without excessive toxicity, irritation, allergic response, or other problem complications commensurate with a reasonable benefit/risk ratio.

In addition to the oil containing SPMs and/or SPM precursors, the nutritional supplements and pharmaceutical and cosmetic formulations might contain other ingredients. For example, in preferred embodiments the SPM and/or SPM precursor containing oils are mixed, dissolved, emulsified (e.g., in oil/water, water/oil, or double emulsions), or suspended in a matrix or base. The matrix or base can, e.g., be an edible oil such as ω-3 PUFA-containing oils, an ω-3 PUFA concentrate containing high levels of EPA, or DHA, or mixtures of EPA and DHA, or another edible oil suitable for consumption or administration. The matrix or base might also be water or an aqueous buffer. The oils containing SPMs and/or SPM precursors might also be prepared in liposomes, nanoparticles, or microparticles.

To enhance shelf life, the supplements and formulations might also contain one or more stabilizers including antioxidants such as one or several tocopherols, ascorbic acid and ascorbyl-fatty acid derivatives, and other antioxidants which are commonly used in the stabilization of dietary oils, such as rosemary extract. The oils might furthermore be packaged in containers that minimize exposure to oxygen, heat, and incident light. These conditions will specifically augment the stability of the SPMs and SPM precursors by preventing or limiting oxidation and isomerization of double bonds. Stability of the bulk oil or the formulated oil will also benefit from these conditions since the SPMs and SPM precursors are dissolved in oils with a significant level of PUFA that are sensitive to oxidation.

The supplements and formulations might also include one or more active ingredients such as aspirin, other non-steroidal anti-inflammatory drugs, vitamins, anti-oxidants, flavonoids, minerals, trace elements, fatty acids, lycopene, S-adenosylmethionine, oleocanthal, resveratrol, pterostilbene, bioactive proteins and peptides such as bromelain, oligosaccharides, glucosinolates, and plant extracts such as *Boswellia serrata*, mangosteen, capsicum, turmeric, ginger, tea, neem, and/or willow bark extract. Ingredients are not limited to the here mentioned examples.

Specific nutritional supplements can be made to support specific health conditions that include a fish oil, a krill oil, or a long-chain ω-3 PUFA concentrate supplemented with an oil containing SPMs or SPM precursors, together with glucosamine and chondroitin for arthritis, or with zinc, lutein and zeaxanthin for eye health.

Other nutritional supplements containing oils with SPMs and SPM precursors are multi-vitamin preparations, sports nutrition, fortified fish oil capsules, oral healthcare products such as tooth paste and mouthwash, and specific oils used as food such as spreads, dressings, cooking oils, snacks, nutritional drinks, soft gels, chewing gums, and in infant formulas.

The oils described herein might be included along with one or more pharmaceutically acceptable carriers or excipients to make pharmaceutical formulations which can be administered by a variety of routes including oral, rectal, vaginal, topical, transdermal, sublingual, subcutaneous, intravenous, intramuscular, insufflation, intrathecal, and intranasal administration. Suitable formulations for use in the present invention are found in Remington's Pharmaceutical Sciences, Mack Publishing Company, Philadelphia, Pa., 17th ed. (1985).

The active ingredient(s) can be mixed with an excipient, diluted by an excipient, and/or enclosed within a carrier which can be in the form of a capsule, sachet, paper or other container. When the excipient serves as a diluent, it can be a solid, semi-solid, or liquid material, which acts as a vehicle, carrier or medium for the active ingredient. The formulations can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, sterile liquids for intranasal administration (e.g., a spraying device), or sterile packaged powders. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The supplements and formulations of the invention can be formulated so as to provide rapid, sustained or delayed release of the active ingredients alter administration to the patient by employing procedures known in the art.

For preparing solid formulations such as tablets, the oil is mixed with a pharmaceutical excipient to form a solid preformulation composition containing a homogeneous mixture of a compound. Tablets or pills may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, acetyl alcohol, and cellulose acetate.

Liquid forms of the formulations include suspensions and emulsions. The formulations may be encapsulated, prepared as a colloid, introduced into the lumen of liposomes, or incorporated in the layers of liposomes. A liquid formulation may also consist of the oil itself, which may be encapsulated.

The oils are preferably formulated in a unit dosage form of the active oil and its ingredient(s). The amount administered to the subject or patient will vary depending upon what is being administered, the purpose of the administration, such as prophylaxis or therapy, the state of the subject or patient, the manner of administration, and the like all of which are within the skill of qualified physicians, dieticians, and pharmacists. In therapeutic applications, formulations are administered to a patient already suffering from a disease in an amount sufficient to cure or at least partially arrest the symptoms of the disease and its complications. Amounts effective for this use will depend on the disease condition being treated as well as by the judgment of the attending clinician depending upon factors such as the severity of the symptoms, the age, weight and general condition of the patient, and the like.

Specific pharmaceutical formulations could be encapsulated oils to be taken orally for the treatment of diseases with an inflammatory component, sustained release formulas, topical formulations for treatment of acne, psoriasis, eczema, rosacea, etc., intravenous formulations based on emulsified oils which are useful as clinical nutrition and parenteral drugs, liposomal preparations, and ti s sue-targeted delivery system s, inhalation formulations, and formulations which can be injected into the central nervous system.

A further embodiment is the formulation of oils containing SPMs and SPM precursors and having anti-inflammatory or resolution-stimulating activity as cosmetics, beauty products, and nutritional cosmetics. These formulations include make-up, skin moisturizers, and specific topical creams such as sunburn and tanning ointments. In particular, the oils being anti-inflammatory and resolution-stimulating and containing SPMs and SPM precursors, might constitute cosmetics which counteract irritation and inflammation at the site of application.

Methods of Use

The invention features methods for treating a subject (e.g., a human being, dog, cat, horse, cow, goat, pig, fish, and other animals) having inflammatory condition or a disease with an inflammatory component by administering to the subject one or more of the oils, supplements, and formulations described herein, in an amount and dosage schedule effective to cure, treat, and/or reduce inflammation in a subject. The therapeutic use of the SPM and/or SPM precursor-containing oils will be primarily directed to treat or prevent any of many possible ailments, disorders, and diseases that include an aspect of inflammation in their etiology or symptoms. The use may furthermore encompass conditions and diseases that have been reported to be ameliorated by increased ingestion of EPA/DHA or fish oils (e.g., hypertriglyceridemia, arrhythmias, or depression). Examples of inflammatory conditions include cardiovascular disease (e.g., atherosclerosis, high blood pressure, hypercholesteremia, hypertriglyceridemia, endothelial hyporeactivity, cardiac infarction, cerebral stroke), aspects of metabolic syndrome (e.g, loss of insulin sensitivity, obesity, hepatic steatosis, cholestasis), neurodegenerative diseases (Alzheimer's disease, Parkinson disease, multiple sclerosis, apraxia), atopic/allergic reactions, cancer, osteoarthritis, rheumatoid arthritis, inflammatory pain, acne, psoriasis, rosacea, asthma, acute lung injury, chronic obstructive pulmonary disease, cystic fibrosis, sepsis, allergic rhinitis, sinusitis, periodontitis, inflammatory bowel disease, Crohn's disease, macular degeneration, dry eye syndrome, gastric ulceration, cancer, and auto-inflammatory disorders. The oils described herein may also be suitable for treating distinct forms of acute and chronic pain and hypersensitivity to physical and chemical stimuli. The oils described herein might also be useful for treating conditions caused by the dysregulation of angiogenesis, platelet aggregation and coagulation, bone growth, tissue healing, blood pressure regulation, haematopoiesis, and lipid homeostasis. The oils described herein might also be useful for lowering the macroscopic and physical signs of inflammation such as swelling, edema, redness, fever, pain, and inflammatory sickness.

The oils described herein, since they contain long chain ω-3 PUFA-derived lipid mediators with anti-inflammatory and pro-resolving activity, may furthermore obviate the need to augment tissue levels of long chain ω-3 PUFA from which these substances may be formed within a subject's body after dietary supplementation.

The oils described herein might also be administered to subjects having increased or abnormal levels of inflammatory markers such as high-sensitivity C-reactive protein (hs-CRP), serum amyloid A, erythrocyte sedimentation rate, soluble adhesion molecules (e.g., E-selectin, P-selectin, intracellular adhesion molecule-1, vascular cell adhesion molecule-1), cytokines (e.g., interleukin-1β, -6, -8, and -10 and tumor necrosis factor-α), fibrinogen, and/or activated white blood cells (e.g., leukocytes with enhanced rates of production of reduced oxygen and nitrogen species; non-spherical neutrophils, and monocytes with increased vacuolization). In this regard, supplements and formulations of the inventions might be used to reduce the levels of one or more of these inflammatory markers by at least 99, 95, 90, 80, 70, 60, or 50%; or to reduce these levels to within ranges considered normal.

The supplements and formulations may also be administered to a subject to prevent inflammation.

EXAMPLES

Example 1: Fractionation of an Omega-3 PUFA Ethyl Ester Oil by Industrial-Scale Supercritical Fluid Chromatography Permits Enrichment of Esterified Precursors of SPMs and Manufacturing of Distinct Oil Fractions with Different Anti-Inflammatory Activity To evaluate the anti-inflammatory activity of distinct fatty acid-ethyl ester oil fractions obtained during supercritical fluid chromatography (SFC) for the industrial-scale manufacturing of EPA-ethyl ester and DHA-ethyl ester concentrates, a murine model of subcutaneous sterile inflammation was established which permitted measuring the effects of orally administered oil fractions on the pro-inflammatory phase of the inflammatory response. Eight consecutively-eluted oil fractions were produced by SFC at industrial scale by fractionation of an intermediate long chain ω-3 fatty acid-ethyl ester concentrate containing 70% EPA-EE and DHA-EE combined, which upon its turn had been obtained by industrial-scale supercritical fluid extraction (SFE). SFC fractionation is carried out in the following way. A raw material tank, previously blanketed with nitrogen, is charged with the long chain ω-3 PUFA ethyl ester concentrate. The tank content is warmed up if necessary and temperature stabilized approximately between 20-40° C. The oil is processed batch-wise by passing it through a chromatographic column. Oil volumes weighing between 7.5 and 9.5 kg are pumped adjusting pressure and temperature at about 110-135 bars and 20-40° C. Carbon dioxide is pumped at the same time at 110-130 bars and between 43.5-45.5° C. Both flows (omega-3 concentrate and carbon dioxide) are injected onto the head of the chromatographic column flowing inside at a pressure between 98-102 bar and a temperature between 43.5-45.5° C. Taking advantage of differences in retention of the components which make up the oil to be separated through the chromatographic column, filled with modified silica stationary phase, different fractions are collected. Total elution times of single fractionation runs are between 40-85 minutes. Eluted material is collected in consecutively-eluted fractions that last between 2-20 minutes. The ratio between mobile phase (supercritical carbon dioxide) and feed (omega-3 concentrate) is between 600-850 Kg solvent/Kg feed.

In order to initiate inflammation, *Escherichia coli* lipopolysaccharide (LPS; serotype 127:B8, purified by trichloroacetic acid extraction, Sigma-Aldrich) was injected subcutaneously as a single dose (5 milligram per kilogram in a 200 microliter volume of sterile salive) in the dorsal hind flank of a mouse (CD1 mice of 9 weeks age and weighing approximately 30 grams, purchased from the Charles River company). Neutrophil infiltration into the site of inflammation was measured non-invasively by bioluminescence emitted by conversion of luminol by the neutrophil enzyme myeloperoxidase (Gross, 2009), permitting assessment of inflammatory changes over a 6 hour time period. The employment of a sub-cutaneous model of inflammation permitted reproducible bioluminescence measurements of neutrophil activity in order to be able to measure statistically significant changes in neutrophil activity upon administration of test substances. Thirty minutes prior to the administration of LPS, 100 microliter of vehicle control (sterile salive), indomethacin (dose; 10 milligram per kilogram), or one of the eight oil fractions obtained by SFC, was administered by gavage, reflecting the oral route (per os, (p.o.)) of administration. The non-steroidal anti-inflammatory compound indomethacin was used as a positive control to confirm that the inflammatory response induced by LPS could be inhibited. FIGS. 1A-H show the effect of a series of consecutively eluted oil fractions (number 1-8, respectively), obtained by industrial-scale SFC fractionation of the intermediate long chain ω-3 fatty acid-ethyl ester concentrate (containing 70% EPA-EE and DHA-EE combined), on acute inflammatory changes occurring subcutaneously in mice induced by subcutaneous (s.c) administration of lipopolysaccharide (LPS). Open circles; inflammation induced by LPS s.c. (n=40). Open squares; indomethacin 10 mg/kg p.o. 30 minutes prior to LPS s.c. (n=6). Open triangles; 100 microliter of each oil fraction number 1-8 depicted in panel A-H, respectively, each administered once by gavage 30 minutes prior to LPS (n=6 per tested oil fraction). Values are mean±standard error of the mean. Statistically significant differences (Student's t-test; P<0.05) in inflammation are indicated by: *(oil fractions given before LPS compared to vehicle given before LPS), # (indomethacin given before LPS compared to vehicle given before LPS), and t (oil fractions given before LPS compared to indomethacin given before LPS).

As shown in FIG. 1, indomethacin inhibited LPS-induced inflammation by 26% after 3 hours and 44% after 6 hours (number of independent observations n=40), in comparison to mice which had received salive instead of indomethacin (n=40). Of interest, fractionation by SFC of an ethyl ester oil containing high levels of long chain ω-3 PUFA-ethyl esters permitted the production of different oil fractions that had markedly distinct activities on inflammation alter oral administration (n=5 for each tested oil fraction). Three oil fractions induced an anti-inflammatory action after oral administration. Oil fraction 1 significantly reduced inflammation by 61% three hours after the start of LPS-induced inflammation, and by 82% at six hours (FIG. 1A). Oil fraction 7 significantly reduced inflammation by 49% after three hours (FIG. 1G). Oil fraction 8 significantly reduced inflammation by 66% alter 90 minutes (FIG. 1H). Oil fractions 2, 3, 4, and 6 did not significantly change the LPS-stimulated inflammatory response (FIG. 1, panels B, C, D and F, respectively). Of interest is that the anti-inflammatory actions of several oil fractions had significantly higher efficacy than the widely used anti-inflammatory compound indomethacin itself, namely oil fractions 1 and 8. Furthermore, the marked anti-inflammatory activity of oil fraction 1 also points to a resolution-stimulating activity that, already after 6 hours, has actively brought back the neutrophilic inflammatory response nearly to the non-inflamed state. The industrial scale SFC fractionation permitted obtaining sufficient functional differentiation such that one oil fraction, 3, potentiated inflammation at the earliest time point, namely a more than doubling of neutrophil activity at 90 minutes, whereafter the extent of the neutrophilic response normalized to the response observed in vehicle-treated animals. This points out that this oil could facilitate a more rapid inflammatory response towards a bacterial infectious stimulus. In summary, the results demonstrate that through the fractionation of a long chain ω-3 PUFA-rich oil it is possible to achieve oil fractions that have distinct activities on the inflammatory response, and that oil fractions are obtained with significant anti-inflammatory activity after oral administration.

Figure 2:
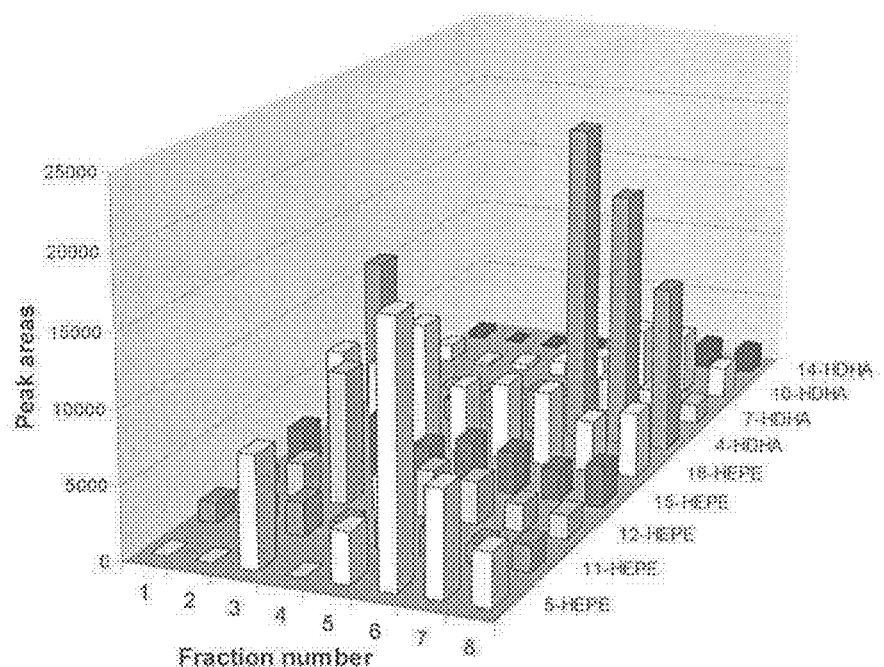
FIG. 2 shows the relative abundance of the ethyl-esterified and saponifiable forms of various monohydroxylated derivatives of the polyunsaturated fatty acids EPA and DHA, in consecutively-eluted oil fractions of an industrial scale SFC fractionation of an intermediate long chain ω-3 PUFA-ethyl ester concentrate (containing 70% EPA-EE and DHA- EE combined). The fractions numbered 1-8 are the same as those tested for anti-inflammatory activity as shown in FIG. 1.

The same oil fractions which had been evaluated for their anti-inflammatory activity were analyzed for their relative or absolute levels of precursors for SPM biosynthesis as well as the SPM themselves. All oils were stabilized by addition of butylated hydroxytoluene in order to avoid inadvertent oxidation. Liquid-liquid extractions of the oil fractions to isolate SPMs and their precursors did not reveal the presence of measurable levels of any mono-, di-, and tri-hydroxylated derivatives of PUFA, such as EPA, DHA, or AA. However, when oils were hydrolyzed by alkaline hydrolysis (10 M NaOH, stirring, 3 hours, at 20° C.), a significant number of lipid mediators derived from EPA, DHA and AA were detected. FIG.2 shows the relative abundance of the ethyl-esterified and saponifiable forms of various monohydroxylated derivatives of the polyunsaturated fatty acids EPA and DHA, in consecutively-eluted oil fractions of an industrial scale SFC fractionation of the intermediate long chain ω-3 fatty acid-ethyl ester concentrate (containing 70% EPA-EE and DHA-EE combined). The fractions numbered 1-8 are the same as those tested for anti-inflammatory activity as shown in FIG. 1. Values are means of duplicate measurements of peak areas of mass spectrometric recordings of ion transitions corresponding to each PUFA derivative. No measurable levels of the corresponding free fatty acid forms of the same PUFA derivatives could be found in these oil fractions. (Abbreviations; HEPE, hydroxy-eicosapentaenoic acid; HDHA, hydroxy-docosahexaenoic acid). Since these oil fractions are derived from ethyl-esterified oil employed in the industrial scale concentration and purification of EPA-EE and DHA-EE, the measured lipid mediators are ethyl esters themselves. Several of the measured compounds are known as intermediate precursors for the formation of SPMs, such as 4-hydroxy-docosahexaenoic acid (4-HDHA;

4-hydroxy-5E,7Z,10Z,13Z,16Z,19Z-docosahexaenoic acid), and 18-hydroxy-eicosapentaenoic acid (18-HEPE; 18S-hydroxy-5Z,8Z,11Z,14Z,16E-eicosapentaenoic acid). 18-HEPE is a precursor for the formation of E-series resolvins, and 4-HDHA is known to have anti-inflammatory and tissue-protective actions in vasoproliferative retinopathy, and may act as a precursor for 4-HDHA-derived SPMs. The various measured SPM precursors distributed differentially into the various oil fractions obtained by SFC. This observation indicates that fractionation of commonly employed ω-3 PUFA-containing oils can permit the manufacturing of oils containing defined presence, combinations, and levels of distinct PUFA-derived lipid mediators.

Figure 3A:
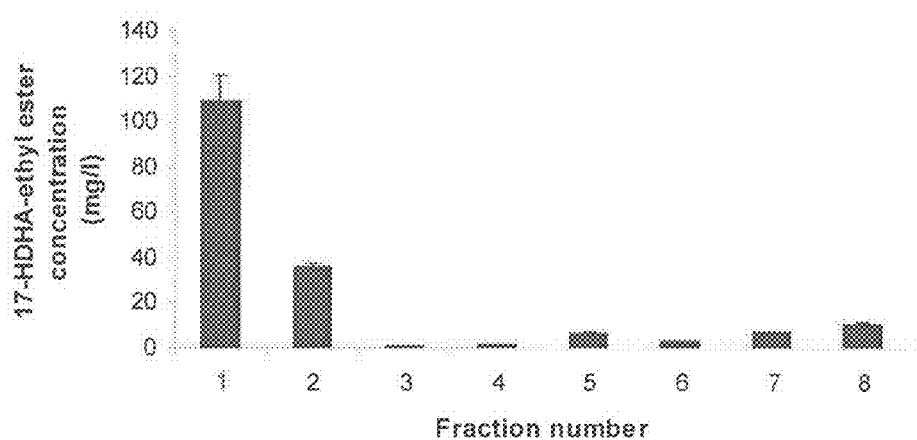
FIG. 3A. shows the concentration of the ethyl ester of the D-series resolvin precursor 17-HDHA in several consecutively eluted oil fractions of industrial scale SFC of an intermediate long chain ω-3 PUFA-ethyl ester concentrate (containing 70% EPA-EE and DHA-EE combined), corresponding to the same fractions as shown in FIGS. 1 and 2.
Figure 3B:
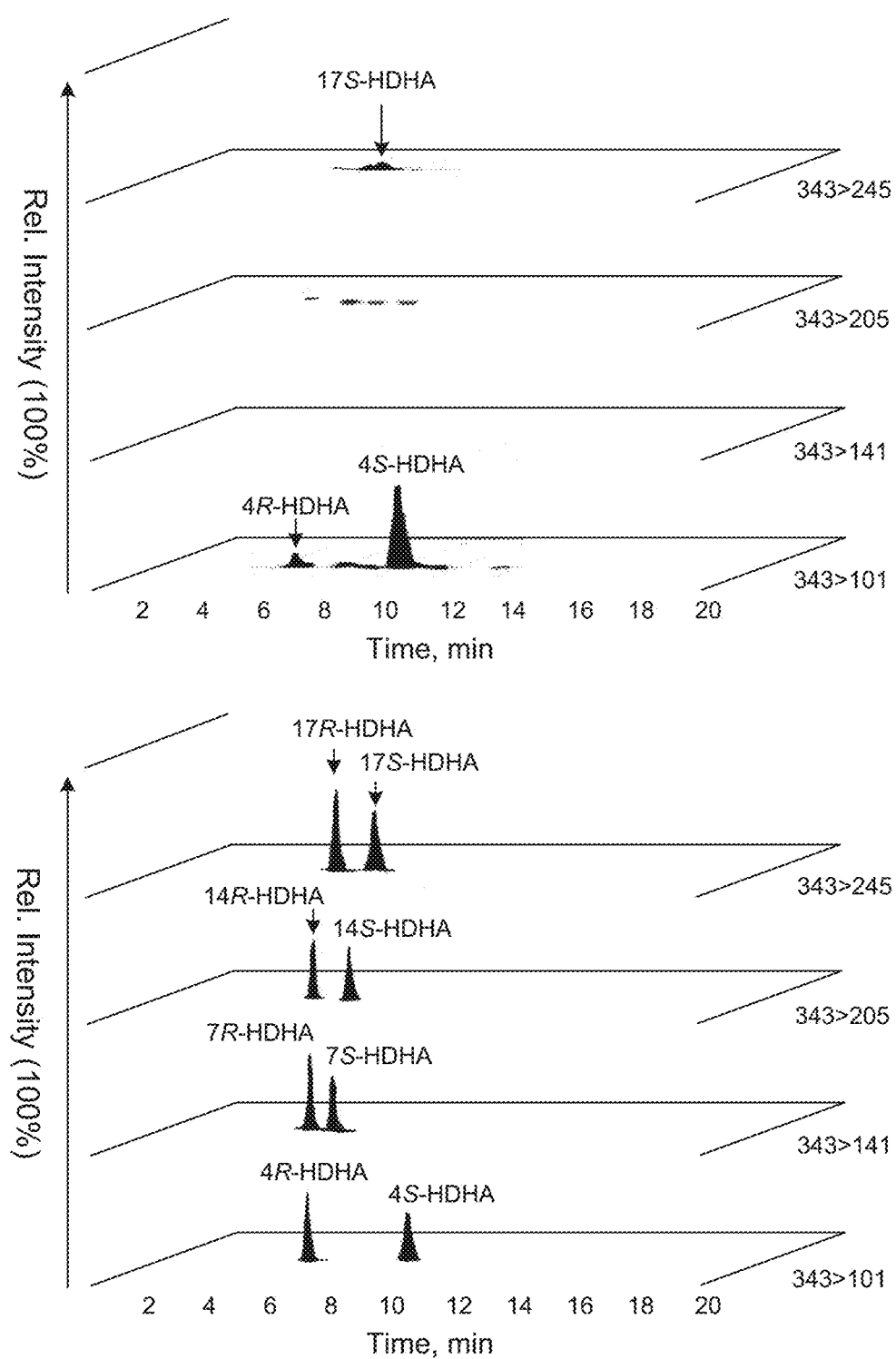
FIG. 3B. shows the results of a chiral high performance liquid chromatography-triple quadrupole mass spectrometric analysis of the 17-HDHA-ethyl ester found enriched in fraction 1, carried out in order to determine the relative abundance of the stereoisomers 17S-HIDHA and 17R-HDHA in the ethyl ester oil fractions 1-8, obtained alter alkaline hydrolysis (top panel).

One derivative of DHA, 17-hydroxy-docosahexaenoic acid (17-HDHA; 17-hydroxy-docosa-4Z,7Z,10Z,13Z,15E, 19Z-hexaenoic acid), is of interest as a precursor for SPM biosynthesis, namely as a central precursor for the formation of the D-series resolvins RvD1, RvD2, RvD3 and RvD4 with potent anti-inflammatory and inflammation resolving bioactivity. FIG. 3A shows the concentration of the ethyl ester of 17-HDHA in several consecutively eluted oil fractions of industrial scale SFC of the intermediate long chain ω-3 fatty acid-ethyl ester concentrate (containing 70% EPA-EE and DHA-EE combined), corresponding to the same fractions as shown in FIGS. 1 and 2. Quantification of 17-HDHA-ethyl ester as a saponifiable substance in the consecutively eluting SFC oil fractions was carried out using internal standards and LC-triple quadrupole mass spectrometry. Values are mean±standard error of the mean (n=3 individual chromatographic separations, measured in duplicate). The results show that 17-HDHA-ethyl ester is enriched in the first eluting fraction, reaching concentrations of approximately 110 mg/l (0.01% w/v). No measurable levels of the corresponding free fatty acid form of 17-HDHA could be found in these fractions. Measurement of 17-HDHA levels in the first oil fraction of several SFC-fractionated lots of this intermediate long chain ω-3 fatty acid-ethyl ester concentrate, which is produced by industrial-scale supercritical fluid extraction (SFE), has indicated that the range of concentrations of 17-HDHA in this fraction lies in the range of 30-110 mg/l. This shows that specific industrial-scale fractionation steps can be devised to enrich specific SPMs and SPM precursors into defined oil fractions.

It was of interest to determine that these SPM precursors found in an ω-3 PUFA-rich oil are of natural origin like the PUFA-ethyl esters themselves in which these substances are dissolved. To that end a chiral high performance liquid chromatography-triple quadrupole mass spectrometric analysis of the 17-HDHA-ethyl ester found enriched in fraction number 1 was carried out in order to determine the relative abundance of the stereoisomers 17S-HDHA and 17R-HDHA (top panel). Oil fraction number 1 analyzed here is the same as oil fraction number 1 shown in FIGS. 1, 2, and 3A. Evaluation of co-migration of the observed lipid mediators with authentic synthetic standards (bottom panel) of the stereoisomers and selected ion monitoring of specific mass transitions by triple quadrupole mass spectrometry indicate that 17-HDHA-ethyl ester in fraction 1 is the natural S stereoisomer. The bottom panel shows the retention times of authentic synthetic standards of the stereoisomers of 17-HDHA, 14-HDHA, 7-HDHA and 4-HDHA. Also 4-HDHA is shown here to be present predominantly as the natural S stereoisomer. Chemical oxidation is not responsible for the 17-HDHA and 4-HDHA present in oil fraction 1, since the products are not racemic. Since the S-stereoisomer of monohydroxylated PUFA is the naturally formed isomer formed by most lipoxygenases, the presence of this stereoisomer in this oil fraction indicates that 17-HDHA and 4-HDHA have a natural origin and are co-extracted and co-purified with long chain ω-3 PUFA all along the industrial process up to the step where SFC fractionation was carried out. Fractionation by a dedicated separation technology, such as supercritical fluid chromatography shown here, furthermore permits the fractionation of select SPMs and SPM precursors of natural origin into specific oil fractions.

Figure 4:
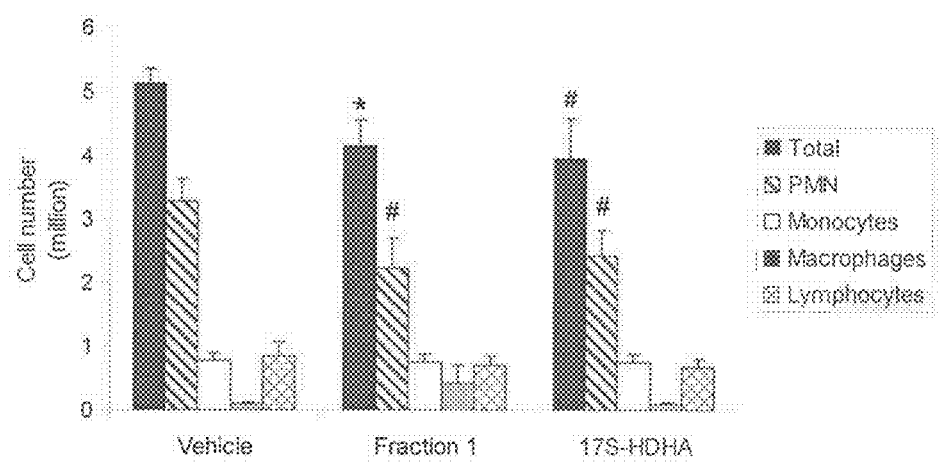
FIG. 4 shows the anti-inflammatory effect of oil fraction 1 and 17S-HDHA administered by gavage in a murine model of peritoneal inflammation induced by intraperitoneal administration of the yeast membrane extract zymosan A.

With respect to 17-HDHA, it is possible that the anti-inflammatory activity of oil fraction 1 (shown in FIG. 1A) can therefore be explained, at least in part, due to the selective enrichment of this anti-inflammatory SPM precursor into this oil fraction. In order to determine the anti-inflammatory action and contribution of 17-HDHA, the anti-inflammatory effect of fraction 1 was determined in a well-known model of sterile inflammation. FIG. 4 shows the anti-inflammatory effect of oil fraction number 1 administered by gavage in a murine model of peritoneal inflammation induced by intraperitoneal administration of the yeast membrane extract zymosan A. Selective changes in specific inflammatory cell populations in the inflammatory exudate 4 hours after initiation of inflammation were determined. Vehicle (100 microliter sterile salive), 100 microliter oil fraction 1, or 1 microgram synthetic 17S-HDHA (Cayman Chemicals) in sterile salive was administered by gavage 30 minutes prior to intraperitoneal injection of 0.1 mg zymosan A. Oil fraction 1 analyzed here is the same as fraction number 1 shown in FIGS. 1, 2, and 3. After 4 hours, the inflammatory exudate was recovered and the changes in the number and types of inflammatory cells determined by fluorescent-activated cell sorting employing specific fluorescently-labeled antibodies. Values are mean±standard error of the mean of 67 individual mice. Statistically significant differences (Student's t-test) are indicated by *(P<0,05) or # (P<0,10) for comparisons of inflammatory exudate cell numbers obtained after treatment with oil fraction 1 or compared to the vehicle-treated mice. As shown in FIG. 4, administration of oil fraction 1 significantly decreased the total number of exudate cells and the number of polymorphonuclear leukocytes (PMN). This anti-inflammatory effect was reproduced by the oral administration (gavage) of 17S-HDHA. No statistically significant changes were measured for monocytes, macrophages or lymphocytes. The result indicate that the anti-inflammatory efficacy upon oral administration of oil fraction 1 containing approximately 100 mg/l (10 microgram in 100 microliter) 17S-HDHA-ethyl ester, is very similar to the anti-inflammatory action of synthetic 17S-HDHA. The results furthermore show that oil fraction 1 has systemic anti-inflammatory efficacy after oral administration in two distinct models of acute inflammation in mice, namely zymosan-initiated peritonitis and sub-cutaneous inflammation induced by lipopolysaccharide.

Example 2: Presence of SPMs and SPM Precursors in Oils of Natural Origin

Figure 5A:
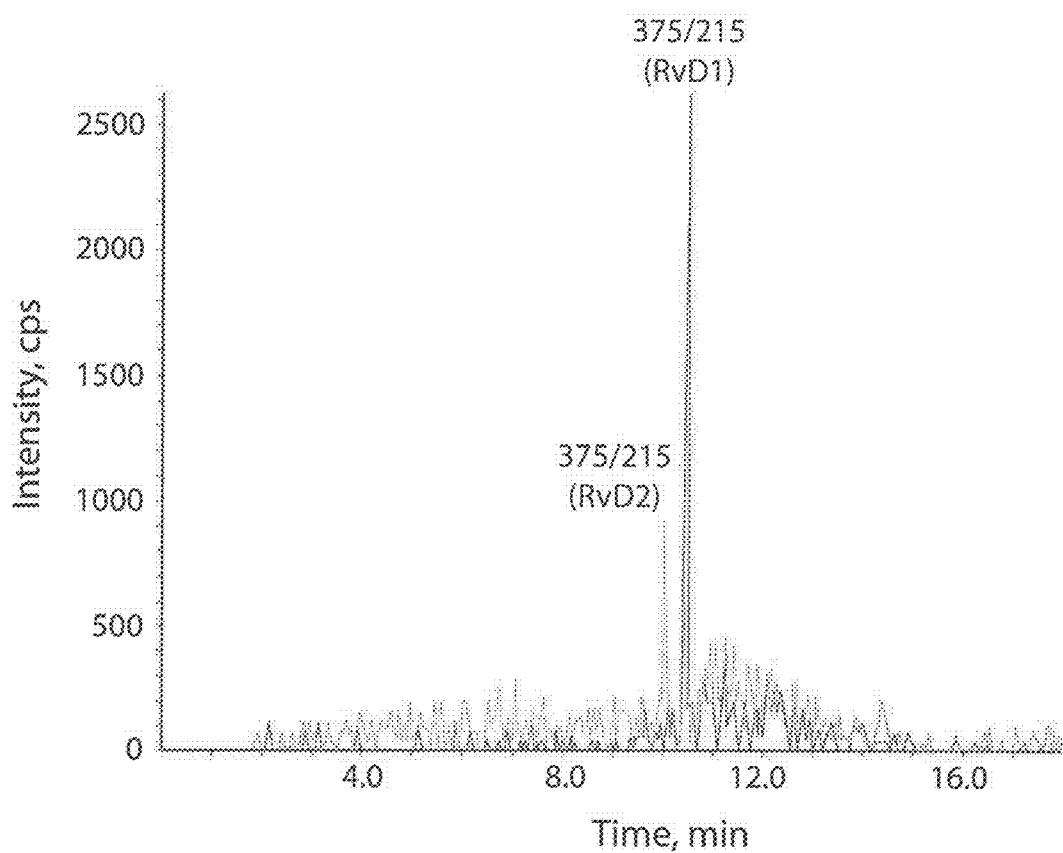
FIGS. 5A-5C show the presence of several specific SPMs and SPM precursors in different oil fractions.

FIG. 5A shows the presence of two resolvins, resolvin D1 and resolvin D2, as saponifiable matter in a crude "1812" fish oil obtained from Peruvian anchovy. This oil is a common raw material which contains approximately 18% EPA and 12% DHA. Anchovy "1812" (18/12 means an oil containing 18% EPA and 12% DHA) oil is the omega-3 fish oil which is currently used in largest volumes world-wide for the manufacturing of refined fish oils and fish oil concentrates which have increased levels of the ω-3 PUFA EPA and DHA. This oil is composed predominantly of triglycerides, indicating that RvD1 and RvD2 are most probably acylated within triglycerides. Alternatively, or in part, these resolvins may also be acylated within a diglyceride or monoglyceride, phosphatidic acid, phospholipid, or other ester or amide species present in this oil. No measurable levels of RvD1 or RvD2 in the free carboxylic acid form were found in this oil. The chromatogram shows that SPMs which are known to possess extremely potent anti-inflammatory and resolution-stimulating activities, are present in long chain ω-3 PUFA containing oils that are widely used in the industry for the manufacturing of long chain ω-3 PUFA-containing oils as nutritional supplements and pharmaceutical ingredients.

Figure 5B:
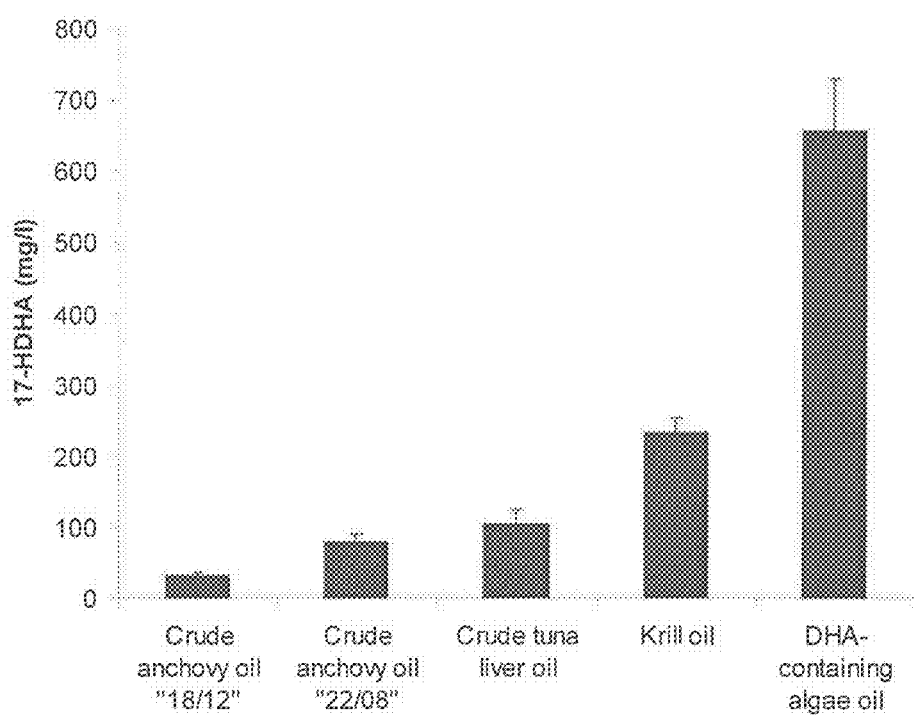

A side-by-side comparison of oils obtained from different long chain ω-3 PUFA-containing organisms, demonstrates that 17-HDHA is present as saponifiable substance in oils from anchovy, tuna, krill, and algae, as shown in FIG. 5B. Two different crude anchovy oils, which are commonly employed as starting material for the preparation of EPA- and DHA-containing fish oils and EPA- and DHA-ethyl ester concentrates, are shown to contain 17-HDHA (18/12 means an oil containing 18% EPA and 12% DHA, 22/08 means an oil containing 22% EPA and 8% DHA). These two exemplary crude oils contain up to 30% EPA and DHA combined, but it is here shown that such oils also contain the SPM precursor 17-HDHA. Measurement of 17-HDHA in tuna, krill and algae oils, which are also widely used as dietary supplements for their content of EPA and DHA, showed that these oils also contained significant levels of 17-HDHA. Also in these oils, the measured 17-HDHA was present in the form of saponifiable substance pointing to the acylated nature of the SPM precursor. The tuna, krill and algae oils are commercially available oils. The tuna oil is a tuna liver oil. The algae oil is a DHA-containing algae oil obtained from a dinoflagellate algae, Order Peridiniida. In particular, these krill and algae oils are extracted from organisms which are purposefully caught or cultured for their relatively high content of DHA, and are shown here to contain relatively high levels of 17-HDHA when compared to the measured fish oils. The presence of this precursor for D-series resolvins demonstrates that oils can be produced with defined levels of SPMs or SPM precursors, and that such oils can be employed for the manufacturing of oils in which these compounds are further enriched.

Figure 5C:
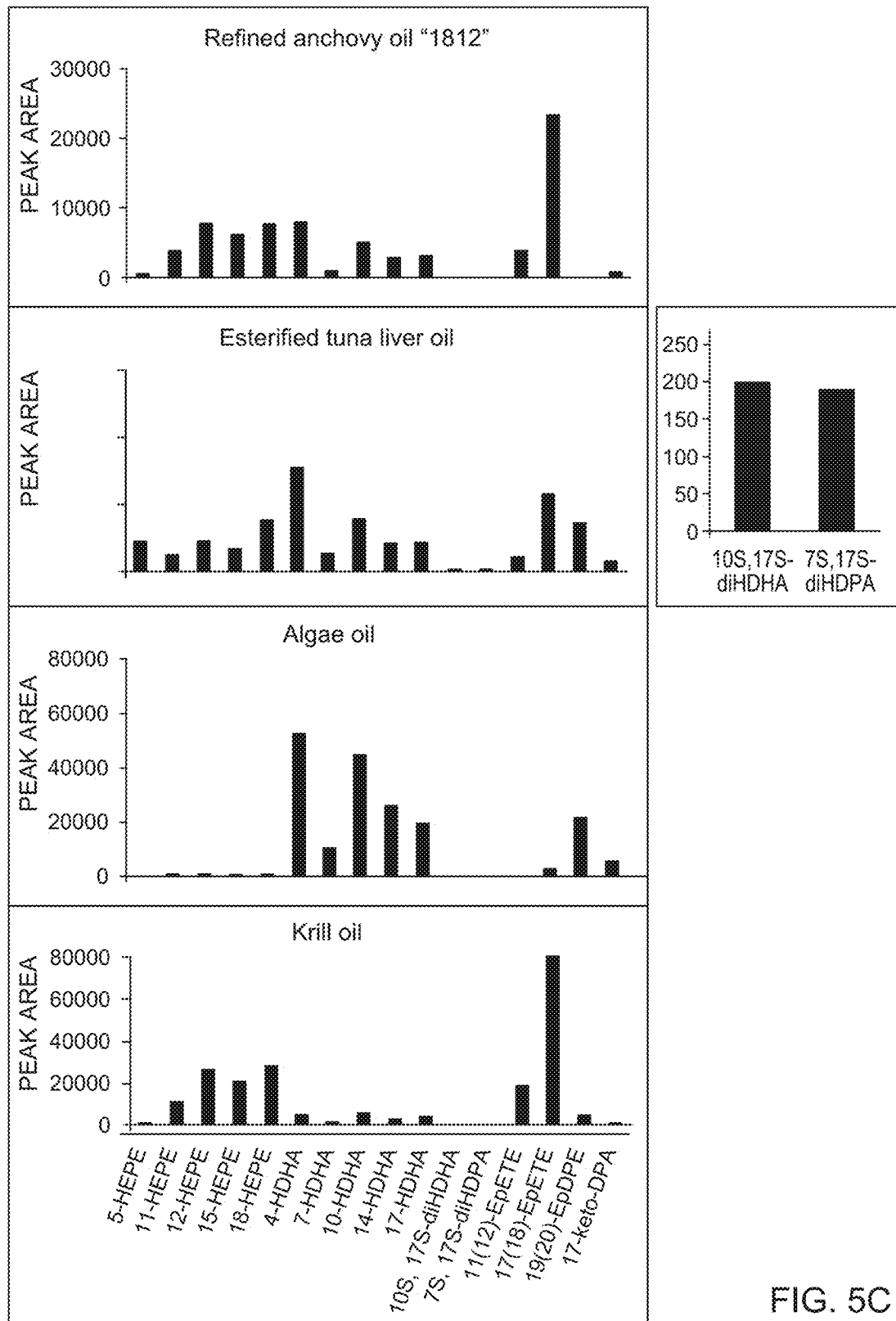

A qualitative profiling of the presence of a number of SPMs and SPM precursors in oils obtained from fish, algae and krill, demonstrated the presence of specific SPMs and SPM precursors in the oils (FIG. 5C). The measurement of the various SPMs and SPM precursors was performed by liquid chromatography-tandem mass spectrometry employing diagnostic transitions and co-elution with commercially available lipid mediator standards. AH compounds detected correspond to saponifiable substances present in the oils, and no corresponding compounds in their free carboxylic acid form were measurable. For example, both EPA- and DHA-derived monohydroxylated SPM precursors and SPMs are present in two fish oils such as a refined "18/12" anchovy oil (containing 18% EPA and 12% DHA) and in an ethyl-esterified tuna liver oil. In contrast, DHA-derived lipid mediators predominate in an oil extracted from algae which are cultured for their high levels of DHA. A krill oil was demonstrated to contain both EPA and DHA-derived mono-hydroxylated lipid mediators, but the EPA-derived compound appear more abundant than the DHA-derived lipid mediators. This was also reflected in the presence of the epoxygenated derivatives, where the DHA-derived SPM 19(20)-epoxy-docosapentaenoic acid (19(20)-EpDPE; 19(20)-epoxy-docosa-4Z,7Z,10Z,13Z,16Z-pentaenoic acid) was the dominant epoxy-derivative in the algae oil, and the EPA-derived SPM 17(18)-epoxy-eicosatetraenoic acid (17 (18)-EpETE; 17(18-epoxy-eicosa-5Z,8Z,11Z,14Z-tetraenoic acid) and 11(12)-epoxy-eicosatetraenoic acid (11(12)-EpETE; 11(12)-epoxy-eicosa-5Z,8Z,14Z,17Z-tetraenoic acid) predominating in the krill oil. Minor components of interest can be identified, such as shown for the tuna liver oil, where the double hydroxylated DHA-derived lipid mediator 10S,17S-dihydroxy-Docosahexaenoic acid (10S, 17S-diHDHA; 10S,17S-dihydroxy-docosa-4Z,7Z,11E,13Z, 15E,19Z-hexaenoic acid), as well as 7,17-dihydroxy-docosapentaenoic acid (ω-3) (7,17-diHDPA (ω-3)); (7S,17S-dihydroxy-docosa-8E,10Z,13Z,15Z,19Z-pentaenoic acid (ω-3)) were found to be present. An oxo derivative of docosapentaenoic acid (ω-3), 17-keto-docosapentaenoic acid (ω-3) (17-keto-DPA) was also detected in all tested oils. Oils obtained from different long chain ω-3 PUFA-containing organisms thus have markedly different composition with respect to SPMs and SPM precursors. Differentiation of oils obtained from long chain ω-3 PUFA-containing organisms based on the content of PUFA-derived lipid mediators is thus possible, and constitutes a valuable base on which to decide which oils might be useful for further fractionation by separation and extraction methods to obtain oils with defined presence, combinations of, and enriched levels of one or more SPMs and SPM precursors.

Example 3: Enrichment of SPMs and SPM Precursors

Figure 6A:
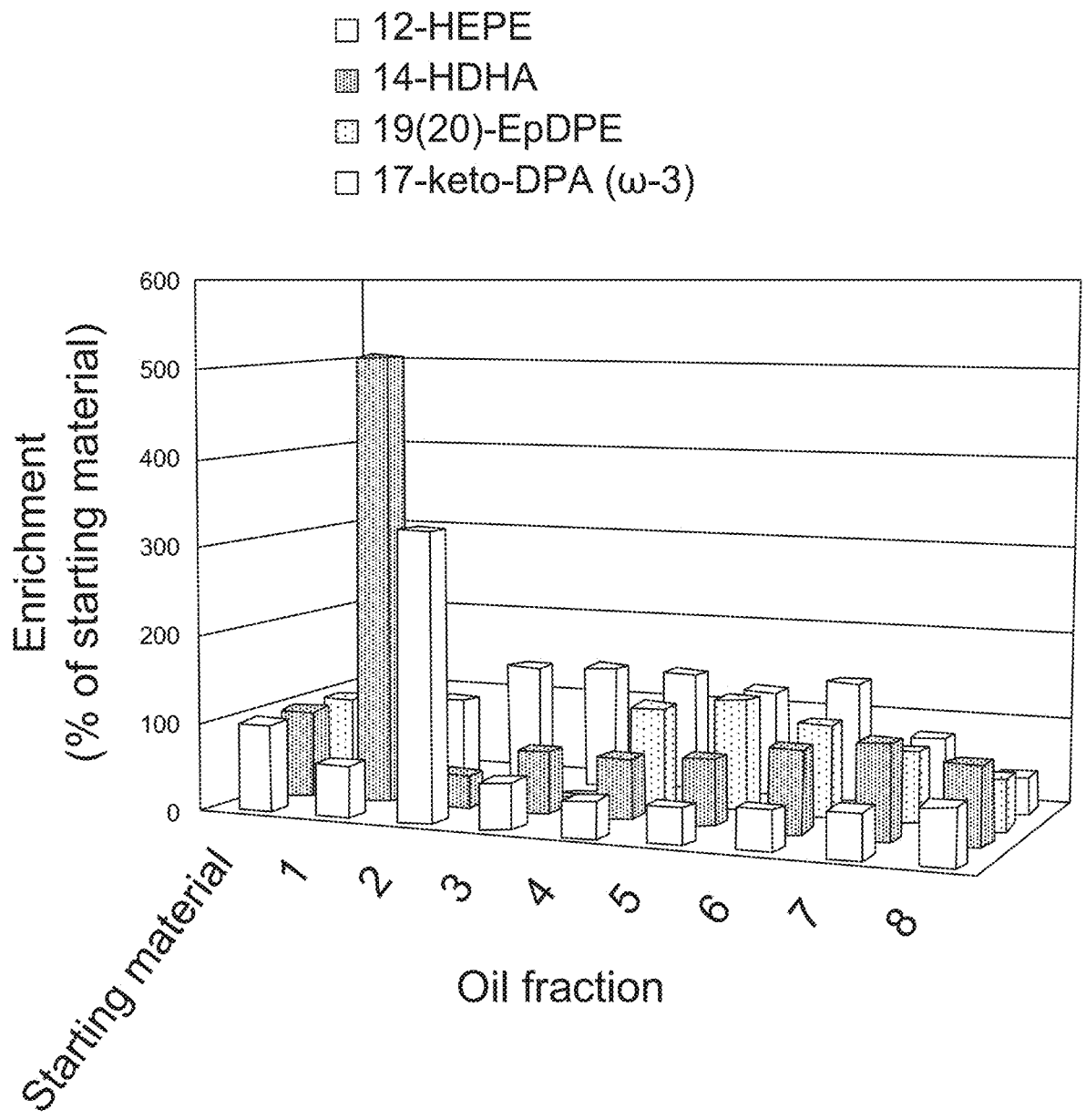
FIGS. 6A-6B, show that selective enrichment of specific SPMs and SPM precursors can be achieved by SFC fractionation of a long chain ω-3 PUFA concentrate.

FIG. 6A shows the selective fractionation of four exemplary oxygenated lipid mediators derived from EPA, DHA, and docosapentaenoic acid (DPA ω-3), into distinct oil fractions. The starting material which was fractionated by SFC into eight consecutive oil fractions was a fatty acid-ethyl ester oil containing 56% EPA-EE plus DHA-EE combined. This oil corresponds to a long chain ω-3 ethyl ester concentrate manufactured from crude oil extracted from a mixture of marine organisms, including marine fish (anchovy, sardine, herring, shad, smelt, salmon, tuna, and bonito) and mollusks (squid, octopus, and cuttlefish). SFC fractionation is carried out in the following way. A raw material tank, previously blanketed with nitrogen, is charged with the omega-3 fatty acid ethyl ester concentrate. The tank content is warmed up if necessary and temperature stabilized approximately between 2040° C. This oil is processed batch-wise by passing it through a chromatographic column. Oil volumes weighing between 9.0 and 12 kg are pumped adjusting pressure and temperature at about 110-135 bars and 20-40° C. Carbon dioxide is pumped at the same time at 110-130 bars and between 43.5-45.5° C. Both flows (omega-3 concentrate and carbon dioxide) are injected onto the head of the chromatographic column flowing inside at a pressure between 98-102 bar and a temperature between 43.5-45.5° C. Taking advantage of differences in retention of the components which make up the oil to be separated through the chromatographic column, filled with modified silica stationary phase, different fractions are collected. Total elution times of single fractionation runs are between 40-85 minutes. Eluted material is collected in eight consecutively-eluted fractions that last between 2-20 minutes. The ratio between mobile phase (supercritical carbon dioxide) and feed (omega-3 concentrate) is between 600-850 Kg solvent/ Kg feed.

The consecutively eluted oil fractions contain different levels of several SPMs and SPM precursora (FIG. 6A), as exemplified by 12-hydroxy-eicosapentaenoic acid (12-HEPE; 12-hydroxy-eicosa-5Z,8Z,10E,14Z,17Z-pentaenoic acid), 14-hydroxy-docosahexaenoic acid (14-HDHA; 14-hydroxy-docosa-4Z,7Z,10Z,12E,16Z,19Z-hexaenoic acid), 19(20)-epoxy-docosapentaenoic acid (19(20)-EpDPE) and 17-keto-docosapentaenoic acid (ω-3) (17-keto-DPA (ω-3)). Values are means of two samples for each oil fraction from two independent industrial scale fractionation runs, measured in duplicate. Results are expressed as percent enrichment compared to the oil which was fractionated. The EPA-derived monohydroxylated lipid mediator 12-HEPE was found to be predominantly present in the second fraction (FIG. 6A). The DHA-derived SPM precursor 14-HDHA was predominantly found in the first fraction. 14-HDHA can be further oxygenated to form, for example, 14,21-dihydroxy-docosahexaenoic acid which has known potent wound healing activity. 14-HDHA can also be further oxygenated to 7S,14S-dihydroxy-docosahexaenoic acid (7S,14 S-dihydroxy-docosa-4Z,8E, 10Z,12E,16Z,19Z-hexaenoic acid) which has anti-inflammatory activity in neutrophilic inflammation. The epoxygenated lipid mediator 19(20)-EpDPE, which is a cytochrome P450 derivative of DHA with anti-inflammatory properties, was found selectively enriched in later eluting fractions, especially in fraction 5. An oxo derivative of docosapentaenoic acid (ω-3), 17-keto-DPA (ω-3), was found to be enriched in fractions 3 to 7. The results indicate that enrichment of one or more specific oxygenated derivatives of EPA, DHA, and DPA (ω-3) can be achieved by SFC fractionation of long chain ω-3 PUFA ethyl ester concentrates. The compounds correspond to saponifiable material, and no corresponding free carboxylic acids were measurable in the oil fractions.

Figure 6B:
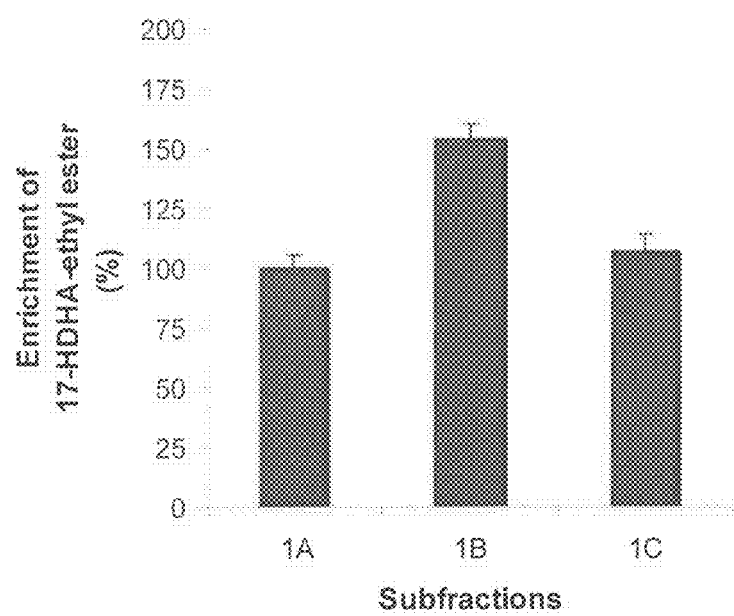

FIG. 6B shows the further enrichment of 17-HDHA-ethyl ester when the first SFC fraction of an intermediate long chain ω-3 fatty acid-ethyl ester concentrate containing 70% EPA-EE and DHA-EE combined is fractionated further. The subfractionated oil corresponds to oil fraction 1 shown in FIGS. 1-3, and which had previously been found to contain enriched levels of the D-series resolvin precursor 17S-HDHA in the form of ethyl ester (FIG. 3A). Further fractionation by SFC into three subfractions eluting between 0 and 2 minutes (fraction 1A), from 2 to 7 minutes (fraction 1B), and from 7 to 12 minutes (fraction 1C), afforded additional enrichment into fraction 1B. Values are the relative levels of 17-HDHA-ethyl ester (means±S.D.) in the three sub-fractions. The results indicate that further enrichment of a specific SPM precursor can be achieved by employing specific separation methods such as SFC.

Figure 7:
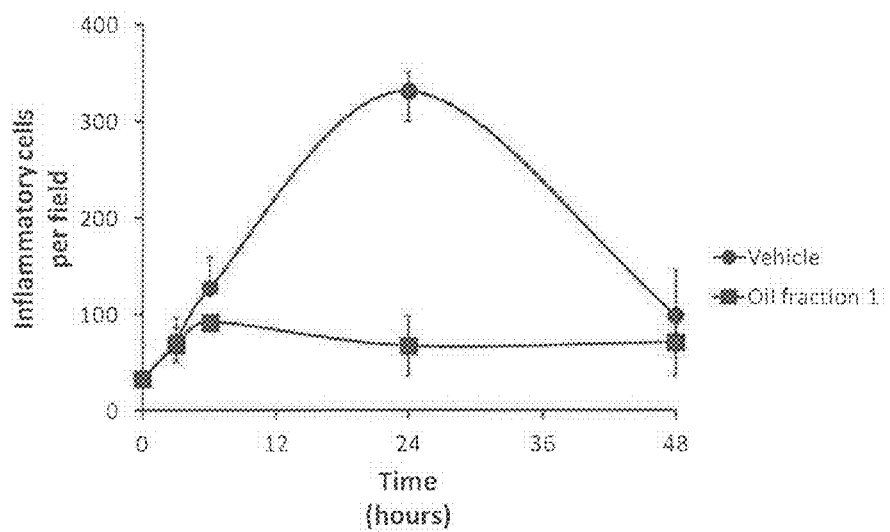
FIG. 7 shows the resolution of inflammation stimulated by a SPM precursor-containing oil.

Example 4: Resolution-Stimulating Activity of an Oil Containing Enriched Level of an SPM Precursor Referring to FIG. 7 which shows the resolution of inflammation stimulated by a SPM precursor-containing oil. The resolution-stimulating (pro-resolving) activity of oil fraction 1 was determined as an example to the capacity of an oil fraction containing an SPM precursor, to activate the resolution of inflammation. FIG. 7 shows the results of an evaluation where the changes in inflammatory cell numbers were measured by histochemistry of subcutaneous fibrin clots formed during the inflammatory response initiated by subcutaneous administration of LPS. Oil fraction 1 or vehicle (sterile salive) in 100 microliter volume was administered by gavage to mice 30 minutes prior to initiation of inflammation by subcutaneous administration of LPS. LPS-induced inflammation employed here was the same model as explained in Example 1. Oil fraction 1 is the first eluting fraction of an industrial-scale SFC fractionation of an intermediate long chain ω-3 PUFA-ethyl ester concentrate containing 70% EPA-EE and DHA-EE combined, and is the same fraction tested in Examples 1-3. This oil fraction 1 corresponds to fraction 1 shown in FIGS. 1-3 and was previously found to contain enriched levels of the D-series resolvin precursor 17S-HDHA in the form of ethyl ester. Subcutaneous fibrin clots were isolated at different time points (3, 6, 24 and 48 hours) during the inflammatory response, and fixated with 4% formaldehyde for 24 hours at 4° C. Glass slides for microscopy with 4 micrometer thick paraffin sections were prepared after tissue dehydration, and stained in modified Wright-Giemsa. Inflammatory cells were counted by microscopy at 400× magnification in full ocular fields of two parts of at least 3 tissue sections per condition. Values are average total inflammatory cell counts per ocular field (mean±S.D.) of 3 individual mice per time point. Inflammatory cell infiltration in control mice reached maximum at 24 hours after administration of LPS, and thereafter inflammation resolved spontaneously towards 48 hours. In mice which had received oil fraction 1 by gavage, the sub-cutaneous inflammation induced by LPS is almost completely resolved (FIG. 7). The SPM-precursor enriched oil fraction, which had already been shown to have a significant anti-inflammatory action on the early neutrophilic pro-inflammatory phase of the inflammatory response (FIG. 1, panel A), is here shown to also have a marked resolution-stimulating (proresolving) activity upon oral administration.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

Arita M, Bianchini F, Aliberti J, Sher A, Chiang N, Hong S, Yang R, Petasis N A,
Serhan C N. Stereochemical assignment, antiinflammatory properties, and receptor for the omega-3 lipid mediator resolvin El. J. Exp. Med. 201, 5, 713-722, 2005.
Bannenberg, G.*, Chiang N*, Ariel A, Anta M, Tjonahen E, Gotlinger K H, Hong S, Serhan C N. Molecular circuits of resolution: formation and actions of resolvins and protectins. J. Immunol 174, 7, 4345-4355, 2005. (*shared first authors)
Bannenberg, G. Serhan, C. N. Specialized pro-resolving lipid mediators in the inflammatory response: An update. Biochim. Biophys. Acta. 1801, 12, 1260-1273, 2010.
Frank D. Gunstone & Fred B. Padley (Editors). Lipid Technologies and Applications, CRC Press, 1 st edition, 1997.
Gladyshev M I, Sushchik N N, Makhutova O N. Production of EPA and DHA in aquatic ecosystems and their transfer to the land. Prostaglandins Other Lipid Mediat. 2013, March 14.
Gross S, Gammon S T, Moss B L, Rauch D, Harding J, Heinecke J W, Ratner L,
Piwnica-Worms D. Bioluminescence imaging of myeloperoxidase activity in vivo. Nat. Med. 15, 4, 455-461, 2009.
Hong S, Tjonahen E, Morgan E L, Lu Y, Serhan C N, Rowley A F. Rainbow trout (*Oncorhynchus mykiss*) brain cells biosynthesize novel docosahexaenoic acid-derived resolvins and protectins-Mediator lipidomic analysis. Prostaglandins Other Lipid Mediat. 78, 1-4, 107-116, 2005.

Martinez, J. L. (Editor). Supercritical Fluid Extraction of Nutraceuticals and Bioactive Compounds, CRC Press, 1st edition, 2007.

Mas E, Croft K D, Zahra P, Barden A, Mori T A. Resolvins D1, D2, and other mediators of self-limited resolution of inflammation in human blood following n–3 fatty acid supplementation. Clin. Chem. 58, 10, 1476-1484, 2012.

Oh S F, Vickery T W, Serhan C N. Chiral lipidomics of E-series resolvins: aspirin and the biosynthesis of novel mediators. Biochim. Biophys. Acta. 1811, 11, 737-747, 2011.

Petrie J R, Shrestha P, Zhou X R, Mansour M P, Liu Q, Belide S, Nichols P D,

Singh S P. Metabolic engineering plant seeds with fish oil-like levels of DHA. PLoS One 7, 11, e49165, 2012.

Pettitt T R, Rowley A F, Secombes C J. Lipoxins are major lipoxygenase products of rainbow trout macrophages. FEBS Lett. 259, 1, 168-170, 1989.

Raatz S K, Golovko M Y, Brose S A, Rosenberger T A, Burr G S, Wolters W R, Picklo M J Sr. Baking reduces prostaglandin, resolvin, and hydroxy-fatty acid content of farm-raised Atlantic salmon (Salmo salary. J. Agrie. Food Chem. 59, 20, 11278-11286, 2011.

Remington. The Science and Practice of Pharmacy, Lippincott Williams & Wilkins, 21st edition, 2005.

Shahidi, F (Ed), Bailey's Industrial Oil and Fat Products, Vol. 1-6, John Wiley & Sons Inc., 6th edition, 2005.

Shearer G C, Harris W S, Pedersen T L, Newman J W. Detection of omega-3 oxylipins in human plasma and response to treatment with omega-3 acid ethyl esters. J. Lipid Res. 51, 8, 2074-2081, 2010.

Wagner K, Inceoglu B, Hammock B D. Soluble epoxide hydrolase inhibition, epoxygenated fatty acids and nociception. Prostaglandins Other Lipid Mediat. 96, 1-4, 76-83, 2011.

Yang R, Chiang N, Oh S F, Serhan C N. Metabolomics-lipidomics of eicosanoids and docosanoids generated by phagocytes. Curr. Protoc. Immunol Ch. 14, Unit 14, 26, 2011.

We claim:

1. A method of reducing cytokine levels in a subject in need thereof, the method comprising administering to the subject an effective amount of a composition comprising 18-hydroxy-eicosapentaenoic acid (18-HEPE), 17-hydroxy-docosahexaenoic acid (17-HDHA, 10-hydroxy-docosahexaenoic acid (10-HDHA), 4-hydroxy-docosahexaenoic acid (4-HDHA, and 14-hydroxy-docosahexaenoic acid (14-HDHA), wherein 17-HDHA is present in the composition in an amount of at least about 100 mg/L, and wherein the composition further comprises eicosapentaenoic acid (EPA), docosahexaenoic acid (DHA), or both.

2. The method of claim 1, wherein the subject has a condition caused by platelet aggregation and coagulation.

3. The method of claim 1, wherein administration of the composition to the subject reduces cytokine levels selected from the group consisting of interleukin-1β (IL-1β), interleukin-6 (IL-6), interleukin-8 (IL-8), and tumour necrosis factor α (TNF-α).

4. The method of claim 1, wherein the subject has abnormal and/or increased cytokine levels in response to an attempt to remove or neutralize a pathogen.

5. The method of claim 1, wherein the subject exhibits a reduction in cytokine levels by at least about 50%.

6. The method of claim 1, wherein the subject exhibits a reduction in cytokine levels by at least about 80%.

7. The method of claim 1, wherein the composition has anti-inflammatory and/or resolution simulating activity.

8. The method of claim 1, wherein 18-HEPE, 17-HDHA, 10-HDHA, 4-HDHA, and 14-HDHA are in the composition as a free fatty acid, ester, phospholipid, mono-glyceride, di-glyceride, tri-glyceride, or combinations thereof.

9. The method of claim 1, wherein the composition further comprises a compound selected from the group consisting of:

resolvin E1 (RvE1; 5S,12R,18R-trihydroxy-eicosa-6Z,8E,10E,14Z,16E-pentaenoic acid), 18S-resolvin E1 (18S-RvE1; 5S,12R,18S-trihydroxy-eicosa-6Z,8E,10E,14Z,16E-pentaenoic acid), 20-hydroxy-RvE 1 (5S,12R,18R,20-tetrahydroxy-eicosa-6Z,8E,10E,14Z,16E-pentaenoic acid), resolvin E2 (RvE2; 5S,18-dihydroxy-eicosa-6E,8Z,11Z,14Z,16E-pentaenoic acid), resolvin E3 (RvE3; 17,18R-dihydroxy-eicosa-5Z,8Z,11Z,13E,15E-pentaenoic acid), 18 S-resolvin E3 (18 S-RvE3; 17,18S-dihydroxy-eicosa-5Z,8Z,11Z,13E,15E-pentaenoic acid), 17,18-epoxy-eicosa-5Z,8Z,11Z,13E,15E-pentaenoic acid, lipoxin $A_5$ (LXA$_5$; 5S,6R,15S-trihydroxy-eicosa-7E,9E,11Z,13E,17Z-pentaenoic acid), 15-epi-lipoxin $A_5$ (LXA5; 5S,6R,15R-trihydroxy-eicosa-7E,9E,11Z,13E,17Z-pentaenoic acid), maresin 1 (MaR1; 7R,14S-dihydroxy-docosa-4Z,8E,10E,12Z,16Z,19Z-hexaenoic acid), 7S-maresin 1 (7S-MaR1; 7S,14S-dihydroxy-docosa-4Z,8E,10E,12Z,16Z,19Z-hexaenoic acid), 7S,14S-diHDHA (7S,14S-dihydroxy-docosa-4Z,8E,10Z,12E,16Z,19Z-hexaenoic acid), protectin D1 (PD1; 10R,17S-dihydroxy-docosa-4Z,7Z,11E,13E,15Z,19Z-hexaenoic acid), 10S,17S-diHDHA (10S,17S-dihydroxy-docosa-4Z,7Z,11E,13Z,15E,19Z-hexaenoic acid), 14S,21S-diHDHA (14S,21S-dihydroxy-docosa-4Z,7Z,10Z,12E,16Z,19Z-hexaenoic acid), 14S,21R-diHDHA (14S,21R-dihydroxy-docosa-4Z,7Z,10Z,12E,16Z,19Z-hexaenoic acid), 14R,21S-diHDHA (14R,21S-dihydroxy-docosa-4Z,7Z,10Z,12E,16Z,19Z-hexaenoic acid), 14R,21R-diHDHA (14R,21R-dihydroxy-docosa-4Z,7Z,10Z,12E,16Z,19Z-hexaenoic acid), 13 S,14 S-epoxy-DHA (13 S,14S-epoxy-docosa-4Z,7Z,9E,11E,16Z,19Z-hexaenoic acid), 16,17S-diHDHA (16,17S-dihydroxy-docosa-4Z,7Z,10Z,12E,14E,19Z-hexaenoic acid), 16,17-epoxy-DHA (16,17-epoxy-docosa-4Z,7Z,10Z,12E,14E,19Z-hexaenoic acid), resolvin D1 (RvD1; 7S,8R,17 S-trihydroxy-docosa-4Z,9E,11E,13Z,15E,19Z-hexaenoic acid), resolvin D2 (RvD2; 7S,16R,17S-trihydroxy-docosa-4Z,8E,10Z,12E,14E,19Z-hexaenoic acid), resolvin D3 (RvD3; 4S,11R,17S-trihydroxy-docosa-5Z,7E,9E,13Z,15E,19Z-hexaenoic acid), resolvin D4 (RvD4; 4S,5,17S-trihydroxy-docosa-6E,8E,10Z,13Z,15E,19Z-hexaenoic acid), resolvin D5 (RvD5; 7S,17 S-dihydroxy-docosa-5Z,8E,10Z,13Z,15E,19Z-hexaenoic acid), resolvin D6 (RvD6; 4S,17S-dihydroxy-docosa-5E,7Z,10Z,14Z,16E,19Z-hexaenoic acid), aspirin-triggered resolvin D1 (AT-RvD1; 7S,8R,17R-trihydroxy-docosa-4Z,9E,11E,13Z,15E,19Z-hexaenoic acid), aspirin-triggered resolvin D2 (AT-RvD2; 7S,16R,17R-trihydroxy-docosa-4Z,8E,10Z,12E,14E,19Z-hexaenoic acid), aspirin-triggered resolvin D3 (AT-RvD3; 4S,11,17R-trihydroxy-docosa-5Z,7E,9E,13Z,15E,19Z-hexaenoic acid),
aspirin-triggered resolvin D4 (AT-RvD4; 4S,5,17R-trihydroxy-docosa-6E,8E,10Z,13Z,15E,19Z-hexaenoic acid),
aspirin-triggered resolvin D5 (AT-RvD5; 7S,17R-dihydroxy-docosa-5Z,8E,10Z,13Z,15E,19Z-hexaenoic acid),
aspirin-triggered resolvin D6 (AT-RvD6; 4S,17R-dihydroxy-docosa-5E,7Z,10Z,14Z,16E,19Z-hexaenoic acid),
7S,17S-diHDPA n–3 (7S,17S-dihydroxy-docosa-8E,10Z,13Z,15Z,19Z-pentaenoic acid (o)-3)),
lipoxin A4 (LXA$_4$; 5S,6R,15S-trihydroxy-eicosa-7E,9E,11Z,13E-tetraenoic acid),
15-epi-lipoxin A4 (15-epi-LXA$_4$; 5S,6R,15R-trihydroxy-eicosa-7E,9E,11Z,13E-tetraenoic acid),
delta12-prostaglandin J$_2$ (delta12-PGJ$_2$; 11-oxo-15S-hydroxy-prosta-5Z,9,12E-trienoic acid),
15-deoxy-delta12,14-prostaglandin J$_2$ (15-deoxy-delta12,14-PGJ$_2$; 11-oxo-prosta-5Z,9,12E,14E-tetraenoic acid),
11(12)-epoxy-eicosatetraenoic acid (11(12)-EpETE; 11(12)-epoxy-eicosa-5Z,8Z,14Z,17Z-tetraenoic acid),
17(18)-epoxy-eicosatetraenoic acid (17(18)-EpETE; 17(18-epoxy-eicosa-5Z,8Z,11Z,14Z-tetraenoic acid),
19(20)-epoxy-docosapentaenoic acid (19(20)-EpDPE; 19(20)-epoxy-docosa-4Z,7Z,10Z,13Z,16Z-pentaenoic acid),
10S,17S-diHDPA n–6 (10S,17S-dihydroxy-docosa-4Z,7Z,11E,13Z,15E-pentaenoic acid),
7,17-diHDPA n–6 (7,17-dihydroxy-docosa-4Z,8E,10Z,13Z,15E-pentaenoic acid), and
7,14-HDPA n–6 (7,14-dihydroxy-docosa-4Z,8E,10Z,12Z,16Z-pentaenoic acid).

10. The method of claim 1, wherein the composition further comprises a compound selected from the group consisting of:
5S-HEPE (5S-hydroxy-eicosa-6E,8Z,11Z,14Z,17Z-pentaenoic acid),
11S-HEPE (11S-hydroxy-eicosa-5Z,8Z,12E,14Z,17Z-pentaenoic acid),
12S-HEPE (12S-hydroxy-eicosa-5Z,8Z,10E,14Z,17Z-pentaenoic acid),
12R-HEPE (12R-hydroxy-eicosa-5Z,8Z,10E,14Z,17Z-pentaenoic acid),
15 S-HEPE (15S-hydroxy-eicosa-5Z,8Z,11Z,13E,17Z-pentaenoic acid),
7S-HDHA (7S-hydroxy-docosa-4Z,8E,10Z,13Z,6Z,19Z-hexaenoic acid),
11S-HDHA (11S-hydroxy-docosa-4Z,7Z,9E,13Z,16Z,19Z-hexaenoic acid),
20S-HDHA (20S-hydroxy-docosa-4Z,7Z,10Z,13Z,16Z,19Z-hexaenoic acid),
17S-HDPAn-6 (17S-hydroxy-docosa-4Z,7Z,10Z,13Z,15E-pentaenoic acid),
14S-HDPAn-6 (14S-hydroxy-docosa-4Z,7Z,10Z,12E,16Z-pentaenoic acid),
17S-HDPAn-3 (17S-hydroxy-docosa-7Z,10Z,13Z,15E,19Z-pentaenoic acid),
14S-HDPAn-3 (14S-hydroxy-docosa-7Z,10Z,12E,16Z,19Z-pentaenoic acid),
10S-HDPAn-6 (10S-hydroxy-docosa-7Z,11E,13Z,16Z,19Z-pentaenoic acid), and
15S-HETE (15S-hydroxy-eicosa-5Z,8Z,11Z,13E-tetraenoic acid).

* * * * *